(12) United States Patent
Benko et al.

(10) Patent No.: US 7,902,233 B2
(45) Date of Patent: Mar. 8, 2011

(54) COMPOUNDS USEFUL AS PESTICIDES

(75) Inventors: Zoltan L. Benko, Indianapolis, IN (US);
David A. Demeter, Fishers, IN (US);
Carl Deamicis, Indianapolis, IN (US);
Lowell Markley, Zionsville, IN (US);
Jack Geno Samaritoni, Avon, IN (US);
Carrie Schmidt, Indianapolis, IN (US);
Yuanming Zhu, Carmel, IN (US); W. Randal Erickson, Carmel, IN (US);
Peter B. Anzeveno, Zionsville, IN (US);
James Todd Pechacek, Indianapolis, IN (US); Gerald B. Watson, Zionsville, IN (US); Gerrit Deboer, Indianapolis, IN (US); Joel J. Sheets, Zionsville, IN (US); Susan Zabik, Cicero, IN (US);
Carla N. Yerkes, Crawfordsville, IN (US); Christian Schobert, Salem, VA (US); James E. Dripps, Carmel, IN (US); Leonard Dintenfass, Indianapolis, IN (US); Laura L. Karr, Lebanon, IN (US); Paul A. Neese, Tucson, AZ (US);
Jim X. Huang, Carmel, IN (US); James M. Gifford, Lebanon, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 12/474,928

(22) Filed: May 29, 2009

(65) Prior Publication Data

US 2009/0318466 A1 Dec. 24, 2009

Related U.S. Application Data

(62) Division of application No. 10/535,653, filed as application No. PCT/US03/41067 on Dec. 19, 2003, now Pat. No. 7,557,132.

(60) Provisional application No. 60/435,928, filed on Dec. 20, 2002.

(51) Int. Cl.
*A61K 31/44* (2006.01)
*C07D 211/82* (2006.01)
(52) U.S. Cl. .................. 514/357; 546/329; 546/330
(58) Field of Classification Search .................. 546/329, 546/330; 564/336; 514/357, 646
See application file for complete search history.

(56) References Cited

OTHER PUBLICATIONS

CAPLUS Accession No. 1932:11638, abstact of Auwers, K. et al, "Ketimide-enamine tautomerism. III. Chemical and spectrochemical methods of determining structure."*

* cited by examiner

*Primary Examiner* — Kamal A Saeed
*Assistant Examiner* — Janet L Coppins
(74) *Attorney, Agent, or Firm* — Ronald S. Maciak; Carl D. Corvin

(57) ABSTRACT

Compounds useful to control pests are provided.

4 Claims, No Drawings

COMPOUNDS USEFUL AS PESTICIDES

PRIORITY

This application claims priority from U.S. provisional application 60/435,928 which was filed on Dec. 20, 2002.

FIELD OF THE INVENTION

This invention provides compounds that are useful as pesticides.

BACKGROUND OF THE INVENTION

There is an acute need for new pesticides. For example, insects and mites are developing resistance to the insecticides and acaricides in current use. At least 400 species of arthropods are resistant to one or more insecticides. The development of resistance to some of the older insecticides, such as DDT, the carbamates, and the organophosphates, is well known. But resistance has even developed to some of the newer pyrethroid insecticides and acaricides. Therefore, a need exists for new insecticides and acaricides, and particularly for compounds that have new or atypical modes of action.

DETAILED DESCRIPTION OF THE INVENTION

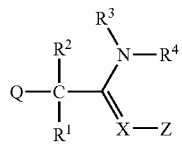

Figure One

In Figure One Q, X, Z, $R^1$, $R^2$, $R^3$, and $R^4$ have the following meanings.

Q can be any five- or six membered carbocyclic or heterocyclic ring, such as, phenyl, pyridyl, pyridazinyl, pyrimidinyl, pyrazinyl, pyrrolyl, pyrazolyl, imidazolyl, thienyl, furanyl, thiazolyl, isothiazolyl, oxazolyl, and isoxazolyl, and including reduced forms of the heterocyclic rings such as tetrahydrofuranyl.

X is N, CR, COR, $CSO_nR$ (where n=0, 1, or 2), $CN(R)_2$, C(C=O), C(C=S)R, C(C=NR)R, $CP(=O)_m(R)_2$ (where m=0 or 1), or $CP(=S)_m(R)_2$ (where m=0 or 1), where each R independently can be
- (a) a $C_{1-10}$, branched or unbranched, alkyl, alkoxy, alkenyl, alkynyl, alkylthio, alkylsulfinyl, alkylsulfonyl, alkylcarbonyl, alkylcarbonothioyl, alkoxycarbonyl, alkylthiocarbonyl, alkoxycarbonothioyl, alkylthiocarbonothioyl, or HC(=NH)—;
- (b) a $C_{3-10}$, cycloalkyl, or cycloalkenyl;
- (c) an aryl, heterocyclyl, aryloxy, heterocyclyloxy, arylthio, heterocyclylthio, arylamino, or heterocyclylamino; or
- (d) a hydro, hydroxy, mercapto, amino, cyano, formyl, nitro, halo, or aminocarbonyl.

Z is CN or $NO_2$.

$R^1$ and $R^2$ each independently can be:
- (a) a $C_{1-10}$, branched or unbranched, alkyl, alkoxy, alkenyl, alkynyl, alkylthio, alkylsulfinyl, alkylsulfonyl, alkylcarbonyl, alkylcarbonothioyl, alkoxycarbonyl, alkylthiocarbonyl, alkoxycarbonothioyl, alkylthiocarbonothioyl, or HC(=NH)—;
- (b) a $C_{3-10}$, cycloalkyl, or cycloalkenyl;
- (c) an aryl, heterocyclyl, aryloxy, heterocyclyloxy, arylthio, heterocyclylthio, arylamino, or heterocyclylamino; or
- (d) a hydro, hydroxy, mercapto, amino, cyano, formyl, nitro, halo, or aminocarbonyl.

$R^1$ and $R^2$ can optionally be linked together with either a bond or a chain of 1-4 atoms, where such atoms can be carbon, nitrogen, sulfur, phosphorus and oxygen.

$R^3$ and $R^4$ each independently can be:
- (a) a $C_{1-10}$, branched or unbranched, alkyl, alkoxy, alkenyl, alkynyl, alkylthio, alkylsulfinyl, alkylsulfonyl, alkylcarbonyl, alkylcarbonothioyl, alkoxycarbonyl, alkylthiocarbonyl, alkoxycarbonothioyl, alkylthiocarbonothioyl, or HC(=NH)—;
- (b) a $C_{3-10}$, cycloalkyl, or cycloalkenyl;
- (c) an aryl, heterocyclyl, aryloxy, heterocyclyloxy, arylthio, heterocyclylthio, arylamino, or heterocyclylamino; or
- (d) a hydro, hydroxy, mercapto, amino, cyano, formyl, nitro, halo, or aminocarbonyl.

$R^2$ and $R^3$ can optionally be linked together with a chain of 1-4 atoms, where such atoms can be carbon, nitrogen, sulfur, phosphorus and oxygen.

$R^3$ and $R^4$ can optionally be linked together with a chain of 1-4 atoms, where such atoms can be carbon, nitrogen, sulfur, phosphorus and oxygen.

Each member of Q, X, R, $R^1$, $R^2$, $R^3$, and $R^4$, which may have a hydrogen atom in a certain position, may instead of having such hydrogen atom, have a:
- (a) a $C_{1-10}$, branched or unbranched, alkyl, alkoxy, alkenyl, alkynyl, alkylthio, alkylsulfinyl, alkylsulfonyl, alkylcarbonyl, alkylcarbonothioyl, alkoxycarbonyl, alkylthiocarbonyl, alkoxycarbonothioyl, alkylthiocarbonothioyl, HC(=NH)—, dialkylphosphonyl, or dialkylphosphatyl;
- (b) a $C_{3-10}$, cycloalkyl, or cycloalkenyl;
- (c) an aryl, heterocyclyl, aryloxy, heterocyclyloxy, arylthio, heterocyclylthio, arylamino, or heterocyclylamino; or
- (d) a hydro, hydroxy, mercapto, amino, cyano, formyl, nitro, halo, or aminocarbonyl;

in such position, provided that these substituents are sterically compatible and the rules of chemical bonding and strain energy are satisfied. Figure One is a generic structure. It should be noted that this generic structure can represent, depending on the substituents used, two generic isomers due to the presence of the double bond. These two generic isomers can exist in a dynamic equilibrium with each other and so interconvert through tautomeric or canonical forms by free rotation around the relevant bond. This invention comprises all such interconverting isomers and purified derivatives thereof. The nature of tautomeric and canonical forms is understood to be as described in "Advanced Organic Chemistry: Reactions, Mechanisms and Structure", $4^{th}$ edition, J. March ed., John Wiley and Sons, New York, 1992.

The term "aryl" means a monovalent radical derived by loss of hydrogen from an aromatic hydrocarbon. The term heterocyclyl means a monovalent radical derived by loss of a hydrogen from an ring structure, where such ring structure contains one or more nitrogen, oxygen, or sulfur atoms. Examples of aryls and heterocyclyls include, but are not limited to, phenyl, naphthyl, pyridyl, pyridazinyl, pyrimidinyl, pyrazinyl, pyrrolyl, pyrazolyl, imidazolyl, thienyl, furanyl, thiazolyl, isothiazolyl, oxazolyl, and isoxazolyl, and included are reduced forms of the heterocyclyl such as tetrahydrofuranyl.

All salts and esters of these compounds are contemplated as part of this invention.

The compounds of the invention are useful for the control pests such as, insects and mites. Therefore, the present invention also is directed to a method for inhibiting an insect or mite, which comprises applying to a locus of the insect or mite an insect- or mite-inhibiting amount of a compound of this invention. In particular, these compounds control insects in the order *Homoptera*, including the families Aphididae (aphids), Aleyrodidae (whiteflies), Delphacidae (planthoppers), and Cicadellidae (leafhoppers). They also control insects in the order Coleoptera (beetles), including the family Chrysomelidae (leaf beetles), as well as Lepidopteran insects such as caterpillars. In particular, other representative pests which may be controlled by the method of this invention include members of the Arthropoda, including mites of the suborders Mesostigmata, Sarcoptiformes, Trombidiformes and Onchychopalpida; sucking and biting lice of the orders Anoplura and Mallophaga: ticks of the families Ixodidae and Argasidae: fleas of the families Pulicidae, Ceratophyllidae, and others; Cimex and other Hemiptera; Triatoma and other Heteroptera: and myiasis-related fly larvae and blood sucking adults (including mosquitoes) of the suborders Brachycera, Cyclorrhapha and Nematocera. Representative also are helminths included in the Nematoda (Strongylida, including but not limited to Strongyloidea, Ancylostomatoidea, Trichostrongyloidea and Metastrongyloidea; Ascarida>*Ascaris*!; Filariina, such as but not limited to Onchocerca and Dirofilaria; Rhabditida; and Trichinellida); Cestoidea, especially Cyclophyllidea, and Trematoda, including Strigeatoidea such as Schistosoma; Echinostomida such as Fasciola; and Plagiorchiida such as Paraqonimus. Other pests which may be controlled by compounds of this invention Acanthocephala such as Macracanthorhynchus, Onicola or Moniliformis, and Pentastomida, especially Linguatula; and Protozoa, especially Coccidia such as Eimeria and Plasmodium, Piroplasmea such as Babesia; Toxoplasmea such as Trypanosoma; Trichomonadidae such as Trichomonas and Entarnoebidae such as Entamoeba. Illustrative of specific pests of various animals which may be controlled by the method of this invention include arthropods such as mites (mesostigmatids, itch. mange, scabies. chiggers), ticks (soft-bodied and hard-bodied), lice (sucking, biting), fleas (dog flea, cat flea, oriental rat flea), true bugs (bed bugs, kissing bugs), bloodsucking adult flies (horn fly, horse fly, stable fly. black fly. deer fly, louse fly, tsetse fly, punkies, mosquitoes). and parasitic fly maggots (bot fly, blow fly, screwworm, cattle grub, fleeceworm); helminths such as nematodes (threadworm, lungworm, hookworm, whipworm, nodular worm. stomach worm, round worm, pinworm, heartworm), cestodes (tapeworms) and trematodes (liver fluke, blood fluke); protozoa such as coccidia, trypanosomes, trichomonads, amoebas and plasmodia; acanthocephalans such as thorny-headed worms; and pentastomids such as tongueworms.

The compounds are useful for reducing populations of insects and mites and are useful in a method of inhibiting an insect or mite population which comprises applying to a locus of the insect or mite an effective insect- or mite-inactivating amount of a compound of this invention.

The "locus" of insects or mites is a term used herein to refer to the environment in which the insects or mites live or where their eggs are present, including the air surrounding them, the food they eat, or objects or materials which they contact. For example, plant-ingesting insects or mites can be controlled by applying the active compound to plant parts that the insects or mites eat, particularly the foliage. Soil-inhabiting insects such as termites can be controlled by applying the active compound to the soil that the insects move through. Insects such as fleas that infest animals can be controlled by applying the active compound to the animal that is infested. Oral administration of the compounds of this invention may be performed by mixing the compound in the animal's feed or drinking water, vitamin or mineral supplement, or by administering oral dosage forms such as drenches, tablets, bolus, salt block or capsules.

It is contemplated that the compounds might also be useful to protect textiles, paper, stored grain, or seeds by applying an active compound to such substance.

The term "inhibiting an insect or mite" refers to a decrease in the numbers of living insects or mites, or a decrease in the number of viable insect or mite eggs. The extent of reduction accomplished by a compound depends, of course, upon the application rate of the compound, the particular compound used, and the target insect or mite species. At least an inactivating amount should be used.

The terms "insect-inactivating amount" and "mite-inactivating amount" are used to describe the amount, which is sufficient to cause a measurable reduction in the treated insect or mite, population. Generally an amount in the range from about 1 to about 1000 ppm by weight active compound is used. In another embodiment, the present invention is directed to a method for inhibiting a insect or mite, which comprises applying to a plant an effective insect or mite inactivating amount of a compound of this invention.

The compounds of this invention are applied in the form of compositions which comprise a compound of this invention and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates.

Effective surfactants, comprising from about 0.5% to about 10% of the wettable powder, are found among the sulfonated lignins, the condensed naphthalenesulfonates, the naphthalenesulfonates, the alkylbenzene-sulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been preformed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

The active compositions may contain adjuvant surfactants to enhance deposition, wetting and penetration of the compositions onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5 percent. Suitable adjuvant surfactants include ethoxylated nonyl phenols, ethoxylated synthetic or natural alcohols, salts of the esters of sulphosuccinic acids, ethoxylated organosilicones, ethoxylated fatty amines, crop oil concentrates containing high molecular weight paraffinic oils and blends of surfactants with mineral and vegetable oils.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations of from −10 ppm to 5000 ppm by weight of compound are expected to provide good control. With many of the compounds, concentrations of from 100 to 1500 ppm will suffice.

The locus to which a compound is applied can be any locus inhabited by an insect or arachnid, for example, vegetable crops, fruit and nut trees, grape vines, and ornamental plants.

Because of the unique ability of mite eggs to resist toxicant action, repeated applications may be desirable to control newly emerged larvae, as is true of other known acaricides.

In addition to being effective against mites and insects when applied to foliage, compounds of this invention have systemic activity. Accordingly, another aspect of the invention is a method of protecting a plant from insects or mites which comprises treating plant seed prior to planting it, treating soil where plant seed is to be planted, or treating soil at the roots of a plant after it is planted, with an effective amount of a compound of this invention.

The action of the inventive compounds can be broadened by adding other, for example insecticidally, acaricidally, and/or nematocidally active, ingredients. For example, one or more of the following compounds can suitably be combined with the compounds of the invention:

(1) organophosphorus compounds such as acephate, azinphosmethyl, cadusafos, chlorethoxyfos, chlorpyrifos, coumaphos, dematon, demeton-S-methyl, diazinon, dichlorvos, dimethoate, EPN, erthoate, ethoprophos, etrimfos, fenamiphos, fenitrothion, fensulfothion, fenthion, fonofos, formothion, fosthiazate, heptenophos, malathion, methamidophos, methyl parathion, mevinphos, monocrotophos, parathion, phorate, phosalone, phosmet, phosphamidon, phosphocarb, phoxim, profenofos, propaphos, propetamphos, prothiofos, pyrimiphos-methyl, pyrimiphos-ethyl, quinalphos, sulprofos; tebupirimphos, temephos, terbufos, tetrachlorvinphos, thiafenox, thiometon, triazophos, and trichlorphon;

(2) carbamates such as aldicarb, bendiocarb, benfuracarb, bensultap, BPMC, butoxycarbocim, carbaryl, carbofuran, carbosulfan, cloethocarb, ethiofencarb, fenobucarb, furathiocarb, methiocarb, isoprocarb, methomyl, oxamyl, pirimicarb, promecarb, propoxur, thiodicarb, and thiofurox;

(3) pyrethroids such as acrinathrin, allethrin, beta-cyfluthrin, bifenthrin, bioresmethrin, cyfluthrin; cyhalothrin; lambda-cyhalothrin; gamma-cyhalothrin, cypermethrin; alpha-cypermethrin; zeta-cypermethrin; deltamethrin, esfenvalerate, fenvalerate, fenfluthrin, fenpropathrin, flucythrinate, flumethrin, fluvalinate, tau-fluvalinate, halfenprox, permethrin, protrifenbute, resmethrin, silafluofen, tefluthrin, tetramethrin, tralomethrin, fish safe pyrethroids for example ethofenprox, natural pyrethrin, tetramethrin, s-bioallethrin, fenfluthrin and prallethrin;

(4) acylureas, other types of insect growth regulators and insect hormone analogs such as buprofezin, chromfenozide, chlorfluazuron, diflubenzuron, fenoxycarb, flufenoxuron, halofenozide, hexaflumuron, hydroprene, leufenuron, methoprene, methoxyfenozide, novaluron, pyriproxyfen, teflubenzuron and tebufenozide, N-[3,5-dichloro-2-fluoro-4-(1,1,2,3,3,3-hexafluoropropoxy)phenyl]-N'(2,6-difluorobenzoyl)urea;

(5) neonicotnioids and other nicotinics such as acetamiprid, AKD-1022, cartap, TI-435, clothianidin, MTI-446, dinotefuran, imidacloprid, nicotine, nitenpyram, thiamethoxam, thiacloprid;

(6) macrolides such as avermectins, milbemycins, or spinosyns for example such as abamectin, ivermectin, milbemycin, emamectin benzoate and spinosad; and (7) other insecticidal, acaricidal, mollscicial and nematocidal compounds or actives such as aldrin, amitraz, azadirachtin, azocyclotin. bifenazate, bromopropylate, chlordimeform, chlorfenapyr, clofentezine, chlorobenzilate, chlordane, cyhexatin, cyromazin, DDT, dicofol, dieldrin, DNOC, endosulfan, ethoxazole, fenazaquin, fenbutatin oxide, fenproximate, beta-fenpyroximate, fipronil, flubenzimine, hexythiazox, IKI-220, indoxacarb, lindane, methiocarb, metaldehyde, methoxychlor, neem, petroleum and vegetable oils, pyridaben, pymetrozine, pyrimidifen, rotenone, S-1812, S-9539, spirodiclofen, sulfur, tebufenpyrad, tetradifon, triazamate, an insect-active extract from a plant; a preparation containing insect-active nematodes, a preparation obtainable from *Bacillus subtilis, Bacillus thuringiensis*, a nuclear polyhedrosis virus, or other like organism genetically modified or native, as well as synergists such as piperonyl butoxide, sesamax, safroxan and dodecyl imidazole, and phagostimulants such as cucurbitacin, sugars and Coax.

EXAMPLES

These examples are provided to further illustrate the invention.

Example A

Preparation of Preparatory Compound A

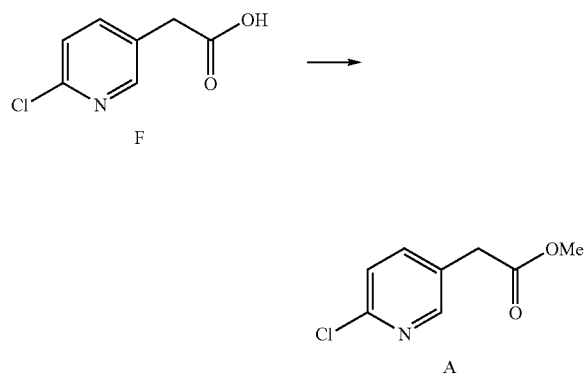

A 2.1 g (12 mmol) portion of Preparatory Compound F dissolved in 70 mL of a 10:1 mixture of ethyl acetate and methanol was carefully treated with 7.0 mL of a 2.0 M solution of trimethylsilyldiazomethane dissolved in hexanes. After vigorous gas formation had subsided, the solvent was removed under reduced pressure to yield 2.5 g (quantitative) of Preparatory Compound A, methyl (6-chloro-3-pyridinyl)acetate, as a brown oil: GCMS: (EI) m/z 185 (M+).

Example B

Preparation of Preparatory Compound B

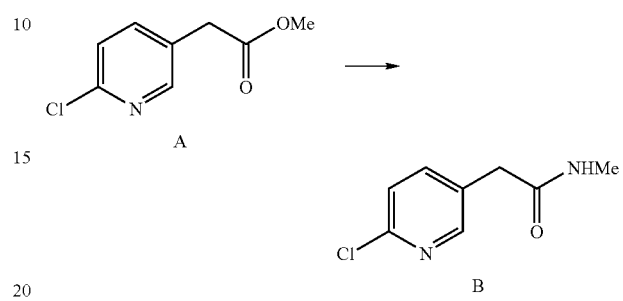

A solution of 1.45 g (7.84 mmol) of Preparatory Compound A in 10 mL of 40% aqueous methylamine in acetonitrile was stirred vigorously at room temperature (about 22° C.) and monitored by reverse-phase chromatography until the reaction was complete. The solvents were removed under reduced pressure and the solid residue dried in a vacuum oven at 50° C. overnight to give 1.39 g (96%) of Preparatory Compound B, 2-(6-chloro-3-pyridinyl)-N-methylacetamide, as a light brown solid: $^1$H NMR (CDCl$_3$) δ 8.30 (d, J=3.0 Hz, 1H), 7.68 (dd, J=3.0 and 8.0 Hz, 1H), 7.34 (d, J=8.0 Hz, 1H), 5.50 (bs, 1H), 3.54 (s, 2H), 2.83 (d, J=4.8 Hz, 3H) ppm. GCMS: (EI) m/z 184 (M+).

Example C

Preparation of Preparatory Compound C

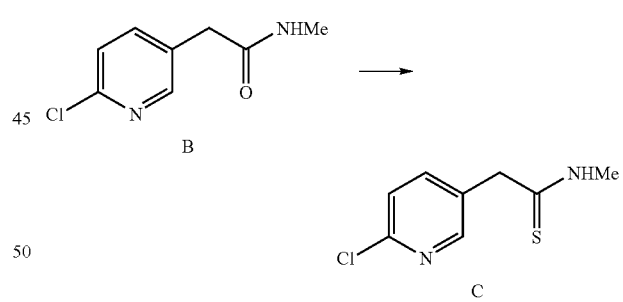

A solution of 714 mg (3.88 mmol) of Preparatory Compound B in 10 mL of pyridine was treated with 0.44 g (0.99 mmol) of phosphorus pentasulfide and heated at 80° C. for 18 hours. The dark mixture was partitioned between dichloromethane and 1M hydrochloric acid and the organic layer dried over sodium sulfate. A portion of silica gel was added and the solvent was removed under reduced pressure. The residue impregnated silica gel was then placed on top of a column of silica gel and eluted with 30-50% ethyl acetate in petroleum ether. The solvent was again removed under reduced pressure to leave 580 mg (75%) of Preparatory Compound C, 2-(6-chloro-3-pyridinyl)-N-methylethanethioamide, as a light yellow solid: mp 140-141° C.; $^1$H NMR (CDCl$_3$) δ 8.25 (d, J=3.0 Hz, 1H), 7.72 (dd, J=3.0 and 8.0 Hz, 1H), 7.33 (d, J=8.0 Hz, 1H), 4.02 (s, 2H), 3.18 (s, 3H) ppm. GCMS: (EI) m/z 200 (M+). Anal. Calcd for $C_8H_9ClN_2S$: C, 47.9; H, 4.52; N, 14.0. Found: C, 48.3; H, 4.51; N, 13.4.

Example D

Preparation of Preparatory Compound D

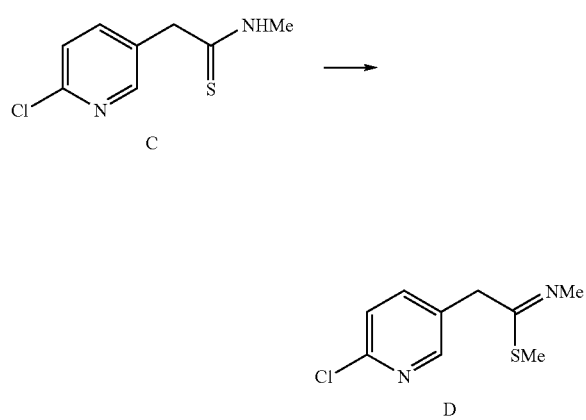

A solution of 370 mg (1.85 mmol) of Preparatory Compound C in 5 mL of dry dimethylformamide was treated with 85 mg (2.1 mmol) of 60% sodium hydride in oil under nitrogen at room temperature (about 22° C.). After gas evolution had subsided, the green solution was treated with 0.2 mL (3.2 mmol) of iodomethane. The mixture was partitioned between water and ether and the organic layer was dried over sodium sulfate. The solvent was removed under reduced pressure and the residue dried further by azeotropic removal of water with dichloromethane to yield Preparatory Compound D, methyl-2-(6-chloropyridin-3-yl)-N-methylpropanimidothioate, as a mixture in mineral oil: GCMS: (EI) m/z 214 (M+).

Example E

Preparation of Preparatory Compound E

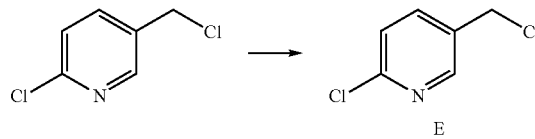

A solution of 5.2 g (32 mmol) of 2-chloro-5-chloromethylpyridine dissolved in 40 mL of ethanol was treated with 20 mL of water and 2.4 g (37 mmol) of potassium cyanide. The mixture was stirred and heated at 50° C. for 20 hours. The dark mixture was then partitioned between dichloromethane and water and the organic layer was washed with brine and dried over sodium sulfate. The solvent was removed under reduced pressure to yield 4.54 g (92%) of Preparatory Compound E, (6-chloro-3-pyridinyl)acetonitrile, as a dark brown liquid: $^1$H NMR (CDCl$_3$) δ 8.38 (d, J=3.0 Hz, 1H), 7.71 (dd, J=3.0 and 7.6 Hz, 1H), 7.42 (d, J=7.6 Hz, 1H), 3.80 (s, 2H) ppm. GCMS: (EI) m/z 152 (M+).

Example F

Preparation of Preparatory Compound F

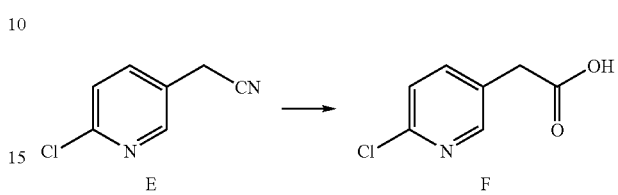

A 4.45 g (29.3 mmol) portion of Preparatory Compound E was treated with 5 mL of concentrated hydrochloric acid. The mixture was stirred and heated at 80° C. for 24 hours. The solution was poured in to ice and the resulting precipitate filtered. Residual water was removed from the sample by treatment with toluene and removal of the azeotrope under reduced pressure. This procedure yielded 3.93 g (78%) of Preparatory Compound F, (6-chloro-3-pyridinyl)acetic acid, as a fine yellow powder: mp 170-171° C.; $^1$H NMR (CDCl$_3$) δ 8.34 (d, J=3.0 Hz, 1H), 7.66 (dd, J=3.0 and 8.0 Hz, 1H), 7.35 (d, J=8.0 Hz, 1H), 3.70 (s, 2H) ppm. MS: (ES+) m/z 172 (M+). Anal. Calcd for $C_7H_6ClNO_2$: C, 49.0; H', 3.52; N, 8.16. Found: C, 49.3; H, 3.53; N, 8.11.

Example G

Preparation of Preparatory Compound G

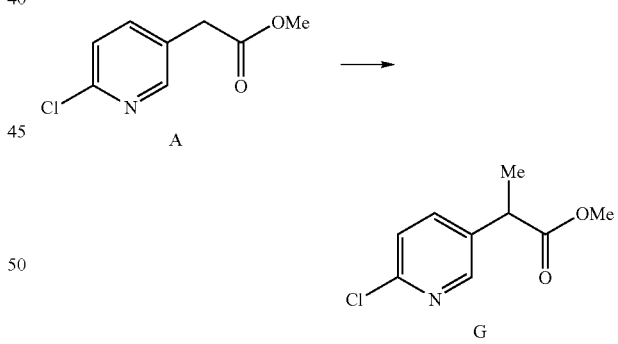

A dry flask was charged with anhydrous tetrahydrofuran (20 mL) and cooled to −78° C. Preparatory Compound A (0.5 g, 0.0027 mol) was added, followed by dropwise addition of n-butyllithium (2.5 M in tetrahydrofuran, 1.2 mL, 0.0029 mol). The resulting mixture was stirred at −78° C. for 10 minutes, then iodomethane (3.45 g, 0.0243 mol) was added dropwise with stirring. The mixture was allowed to slowly warm to room temperature (about 22° C.) and stirred at room temperature for 18 hours. The resulting solution was dissolved in dichloromethane, washed with saturated aqueous ammonium chloride, and dried over magnesium sulfate. The solution was concentrated to yield 0.54 g of crude Preparatory Compound G, methyl 2-(6-chloro-3-pyridinyl)propanoate, as a dark yellow liquid (90% purity).

Example H

Preparation of Preparatory Compound H

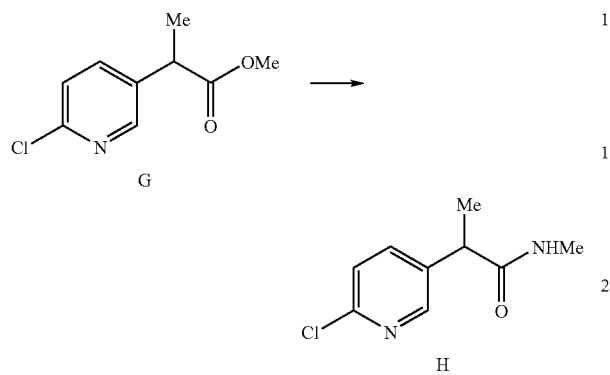

A solution of 1.50 g (7.51 mmol) of Preparatory Compound G in 10 mL of 40% aqueous methylamine was stirred vigorously at room temperature (about 22° C.) and monitored by reverse-phase chromatography until the reaction was complete. The solvents were removed under reduced pressure and the solid residue dried in a vacuum oven at 50° C. overnight to give 1.48 g (quantitative) of Preparatory Compound H, 2-(6-chloro-3-pyridinyl)-N-methylpropanamide, as a white solid: mp 91-93° C.; $^1$H NMR (CDCl$_3$) δ 8.28 (d, J=3.0 Hz, 1H), 7.74 (dd, J=3.0 and 8.0 Hz, 1H), 7.30 (d, J=8.0 Hz, 1H), 3.50 (q, J=6.4 Hz, 1H), 2.78 (d, J=4.8 Hz, 3H), 1.52 (d, J=6.4 Hz, 3H) ppm. GCMS: (EI) m/z 198 (M+). Anal. Calcd for C$_9$H$_{11}$ClN$_2$O: C, 54.4; H, 5.58; N, 14.1. Found: C, 54.1; H, 5.60; N, 13.8.

Example I

Preparation of Preparatory Compound I

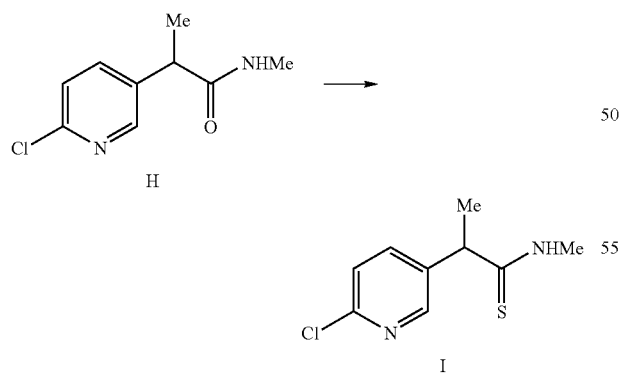

A solution of 1.48 g (7.47 mmol) of Preparatory Compound H in 20 mL of pyridine was treated with 0.87 g (1.96 mmol) of phosphorus pentasulfide and heated at 80° C. for 18 hours. The dark mixture was partitioned between dichloromethane and 1M hydrochloric acid and the organic layer dried over sodium sulfate. A portion of silica gel was added and the solvent was removed under reduced pressure. The residue impregnated silica gel was then placed on top of a column of silica gel and eluted with 30-50% ethyl acetate in petroleum ether. The solvent was again removed under reduced pressure to leave 1.27 g (79%) of Preparatory Compound I, 2-(6-chloro-3-pyridinyl)-N-methylpropanethioamide, as a light yellow solid: mp 130-131° C.; $^1$H NMR (CDCl$_3$) δ 8.26 (d, J=3.0 Hz, 1H), 7.88 (dd, J=3.0 and 8.0 Hz, 1H), 7.32 (d, J=8.0 Hz, 1H), 4.02 (q, J=7.4 Hz, 1H), 3.14 (d, J=5.6 Hz, 3H), 1.66 (d, J=7.4 Hz, 3H) ppm. GCMS: (EI) m/z 214 (M+). Anal. Calcd for C$_9$H$_{11}$ClN$_2$S: C, 50.3; H, 5.16; N, 13.0. Found: C, 50.0; H, 5.13; N, 12.6.

Example J

Preparation of Preparatory Compound J

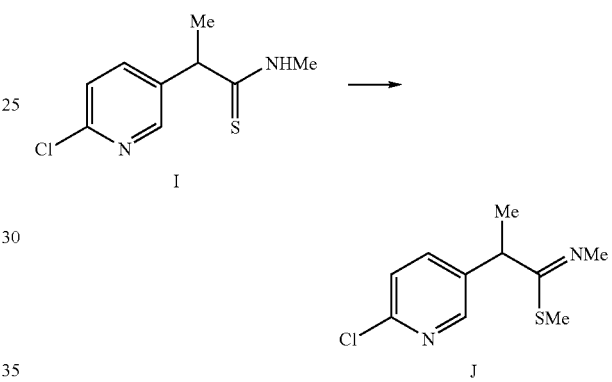

A solution of 162 mg (0.76 mmol) of Preparatory Compound I in 5 mL of dry dimethylformamide was treated with 36 mg (0.90 mmol) of 60% sodium hydride in oil under nitrogen at room temperature (about 22° C.). After gas evolution had subsided, the green solution was treated with 0.25 mL (4.0 mmol) of iodomethane. The mixture was partitioned between water and ether and the organic layer was dried over sodium sulfate. The solvent was removed under reduced pressure and the residue dried further by azeotropic removal of water with dichloromethane to yield Preparatory Compound J, methyl 2-(6-chloro-3-pyridinyl)-N-methylpropanimidothioate, as a mixture in mineral oil: GCMS: (EI) m/z 228 (M+).

Example K

Preparation of Preparatory Compound K

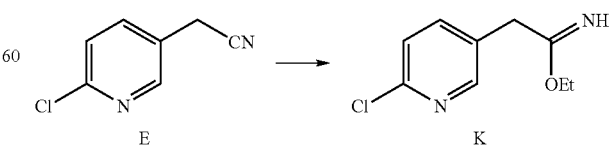

To a solution at −5° C. of 44 mL of absolute ethanol in 155 mL of chloroform under nitrogen was added dropwise 45 mL of acetyl chloride. After 0.5 hours a solution of 8.46 g (55.4 mmol) of Preparatory Compound E in 71 mL of chloroform was added dropwise keeping the temperature at 0° C. or below. The mixture was then kept at 0° C. for 4 hours and was then allowed to warm to room temperature overnight (about 22°). Ethyl ether was added (350 mL) with cooling and the mixture was stirred for several minutes and was then filtered through a medium porosity sintered glass funnel always careful to keep a layer of ether over the white solid. After washing with an ample amount of ether, the solid/ether mixture was washed into a 1 L three-neck round-bottomed flask fitted with a mechanical stirrer and was then diluted with 400 mL of ether and was treated dropwise with 12.34 g (122 mmol, 2.2 equiv.) of triethylamine in ether while cooling. The contents were stirred overnight under nitrogen. The mixture was filtered, the filtrate was dried over sodium sulfate and was concentrated to give 9.91 g (90%) of Preparatory Compound K, ethyl 2-(6-chloro-3-pyridinyl)ethanimidoate, as an oil.

Example L

Preparation of Preparatory Compound L

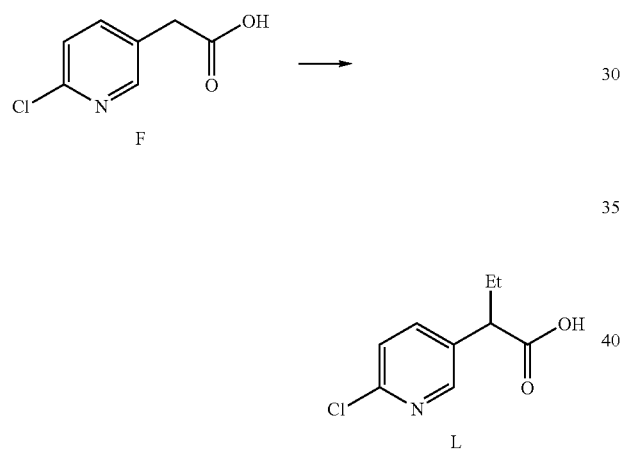

A stirring solution of 3.00 g (17.5 mmol) of Preparatory Compound F in dry dimethylformamide was cooled to −78° C. and treated dropwise with 21.0 mL of 2.5M n-butyllithium in hexanes under a nitrogen atmosphere. This solution was then treated with 7.0 mL (88 mmol) of ethyl iodide in one portion. The mixture was allowed to warm to room temperature (about 22° C.) and then partitioned between dichloromethane and 1M hydrochloric acid, dried over sodium sulfate and the solvent removed under reduced pressure. The resulting dark yellow oil was purified by dissolving in aqueous sodium bicarbonate, washing with diethyl ether, and acidifying with hydrochloric acid. The resulting cloudy aqueous solution was then extracted with dichloromethane, dried over sodium sulfate and the solvent removed under reduced pressure to yield 1.90 g (55% of Preparatory Compound L, 2-(6-chloro-3-pyridinyl)butanoic acid, as a yellow oil: $^1$H NMR (CDCl$_3$) δ 8.34 (d, J=2.8 Hz, 1H), 7.68 (dd, J=2.8 and 8.5 Hz, 1H), 7.32 (d, J=8.5 Hz, 1H), 3.50 (t, J=6.9 Hz, 1H), 2.16 (m, 1H), 1.82 (m, 1H) 0.96 (t, J=6.9 Hz, 3H) ppm.

GCMS: (EI) m/z 199 (M). Anal. Calcd for C$_9$H$_{10}$ClNO$_2$: C, 54.2; H, 5.05; N, 7.02. Found: C, 53.9; H, 4.83; N, 6.93.

Example M

Preparation of Preparatory Compound M

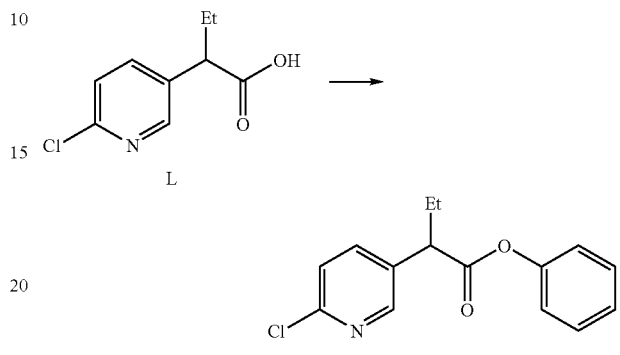

A solution of 2.2 g (11 mmol) of Preparatory Compound L in 100 mL of dichloromethane was treated with 1.5 g (16 mmol) of phenol, 11 mL of a 1.0 M solution of dicyclohexylcarbodiimide in dichloromethane and 0.14 g (1.1 mmol) 4-dimethylaminopyridine. The reaction mixture was stirred for 3 hours at room temperature (about 22° C.) and then diluted with ether and the precipitate removed by filtration through a bed of Cellite. The organic solution was washed with water, dried over sodium sulfate and the solvent removed under reduced pressure. The resulting residue was dissolved in acetonitrile and the solids removed by filtration through a bed of Cellite. The solvent was removed under reduced pressure to yield approximately 3.0 g of Preparatory Compound M, phenyl 2-(6-chloro-3-pyridinyl)butanoate, as a yellow oil.

Example N

Preparation of Preparatory Compound N

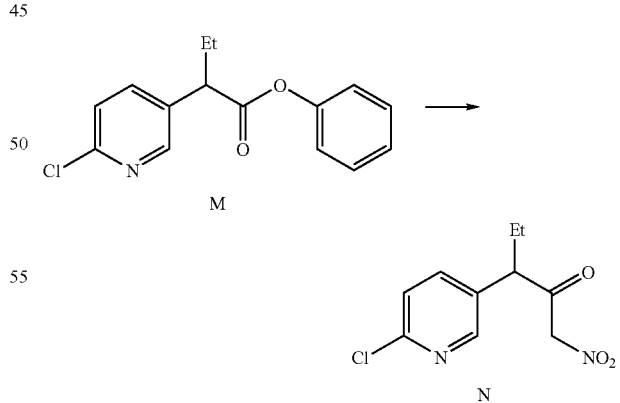

A solution of 3.67 g (32.8 mmol) of potassium t-butoxide in 30 mL of dry dimethylsulfoxide was cooled with an ice bath and treated with 1.77 mL (32.8 mmol) of nitromethane dropwise such that the temperature was maintained at approximately 20° C. After 45 min, a solution of Preparatory Compound M in a few mL of dry dimethylsulfoxide was added and the reaction mixture stirred for 5.5 hours. The reaction mixture was then quenched with a few mL of water and 1 g of urea. While cooling with ice, the pH was adjusted to approximately 1 using 1M hydrochloric acid. The mixture was then extracted with diethyl ether, the organic layer dried over sodium sulfate and the solvent removed under reduced pressure. The residue was purified by reverse phase preparative HPLC using a Waters AMQ column and a 50% acetonitrile/water mixture with 0.1% phosphoric acid as the eluent. The isolated fraction was extracted with dichloromethane, the organic layer dried over sodium sulfate and the solvent removed under reduced pressure to give 1.40 g (53%) of Preparatory Compound N, 3-(6-chloro-3-pyridinyl)-1-nitro-2-pentanone, as a yellow oil: $^1$H NMR (CDCl$_3$) δ 8.28 (d, J=3.2 Hz, 1H), 7.56 (dd, J=3.2 and 8.5 Hz, 1H), 7.38 (d, J=8.5 Hz, 1H), 5.24 (dd, J=16 and 28 Hz, 2H), 3.68 (dd, J=7.9 and 9.5 Hz, 1H), 2.16 (m, 1H), 1.80 (m, 1H), 0.90 (t, J=7.7 Hz, 3H) ppm. MS: (ES−) m/z 241 (M−1).

Example O

Preparation of Preparatory Compound O

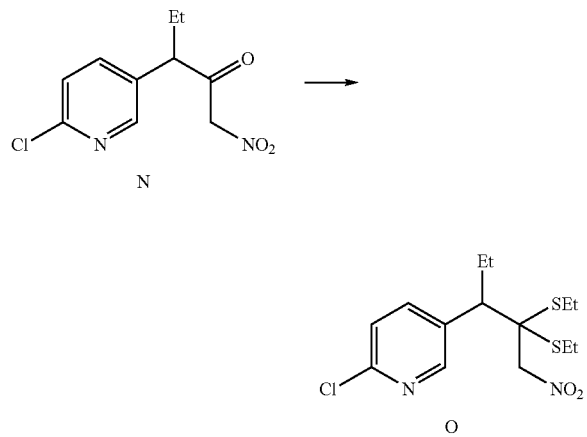

A solution of 0.70 g (2.9 mmol) Preparatory Compound N in 5 mL of ethanethiol was treated with 1.94 g (14.3 mmol) of zinc chloride and the thick slurry allowed to stir 18 hours. After 18 hours, the slurry had turned into a clear orange viscous solution. The reaction mixture was treated with water and extracted exhaustively with dichloromethane. The organic layer was dried over sodium sulfate and the solvent removed under reduced pressure to give 0.70 g of a yellow syrup that was a mixture of products containing Preparatory Compound O, 2-chloro-5-[1-ethyl-2,2-bis(ethylthio)-3-nitropropyl]pyridine.

Example P

Preparation of Preparatory Compound P

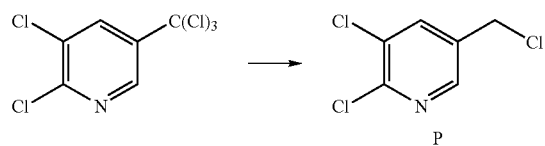

2,3-dichloro-5-trichloromethylpyridine (36.60 g, 0.139 mol) was added to a flask containing acetic acid (53.50 g, 0.892 mol) and methanol (200 mL). The mixture was cooled to −5° C., and zinc dust (20.01 g, 0.308 mol) was added in small portions at 10 minute intervals. The mixture was stirred mechanically for 4 hours, filtered, and concentrated in vacuo. The residue was dissolved in dichloromethane and washed with brine, followed by saturated aqueous sodium bicarbonate, followed by a second brine wash. The organic phase was dried over magnesium sulfate and concentrated in vacuo to yield 21.55 g (79%) of Preparatory Compound P, 2,3-dichloro-5-(chloromethyl)pyridine, as a yellow liquid (about 65% purity). $^1$H NMR δ 8.31 (d, 1H, J=2.3 Hz), 7.85 (q, 1H, J=0.4 Hz and J=2.2 Hz), 4.56 (s, 2H). MS (ESI) m/z 199 ([M+4]$^+$, 8), 197 ([M+2]$^+$, 27), 195 ([M]$^+$, 28), 164 (11), 162 (66), 160 (100), 124 (19)

Example Q

Preparation of Preparatory Compound Q

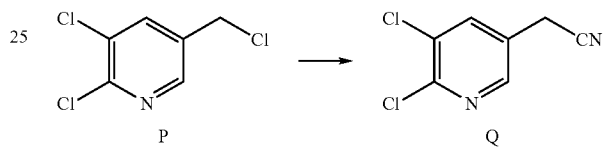

Potassium cyanide (0.47 g, 0.00714 mol) was added to a flask containing Preparatory Compound P in ethanol (25 mL). The mixture was heated at reflux overnight. The mixture was dissolved in dichloromethane and washed twice with water. The organic phase was dried over magnesium sulfate and concentrated in vacuo to obtain a reddish oil. The oil was purified by silica gel chromatography using 50% ethyl acetate/hexanes as eluents. Fractions containing the desired product were isolated and concentrated in vacuo to yield Preparatory Compound Q, (5,6-dichloropyridin-3-yl)acetonitrile, as a purple solid. (0.450 g, 39%). $^1$H NMR δ 8.28 (d, 1H, J=2.1 Hz), 7.83 (dd, 1H, J=0.7 Hz and J=1.6 Hz), 3.78 (s, 2H). MS (ESI) m/z 190 ([M+4]$^+$, 10), 188 ([M+2]$^+$, 64), 186 ([M]$^+$, 99), 151 (100), 124 (39).

Example R

Preparation of Preparatory Compound R

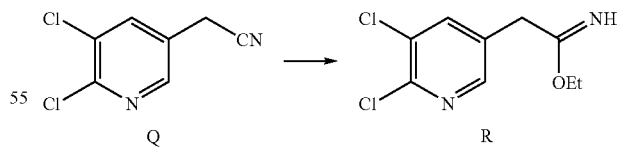

Acetyl chloride (5.29 g, 0.0674 mol) was added dropwise to a flask containing ethanol (4.8 mL) in chloroform (17 mL) at 0° C. The mixture was stirred at 0° C. for 15 minutes, then a solution of Preparatory Compound Q (1.10 g, 0.00591 mol) in chloroform (17.5 mL) was added dropwise. The mixture was stirred for 5 hours at 0° C., during which time a pale precipitate formed, then allowed to slowly warm to room temperature (about 22°). The mixture was stirred at room temperature overnight then 40 mL of ethanol was added to the flask, and the off-white precipitate was collected in a sintered glass funnel and washed several times with diethyl ether, keeping a thin layer of solvent over the material at all times. The solid was washed over into a round-bottomed flask with diethyl ether, and triethylamine (0.66 g, 0.00650 mol) was added. The mixture was stirred at room temperature overnight. The resulting mixture was filtered through a sintered glass funnel. The filtrate was dried over sodium sulfate and concentrated in vacuo to yield 0.930 g (68%) of Preparatory Compound R, ethyl-2-(5,6-dichloropyridin-3-yl)ethanimidoate, as a dark orange oil. $^1$H NMR δ 8.19 (d, 1H, J=2.3 Hz), 7.69 (s, 1H), 4.13 (br s, 2H), 3.54 (s, 2H), 1.30 (t, 3H, J=7.1 Hz). MS (ESI) m/z 236 ([M+4]$^+$, 2), 234 ([M+2]$^+$, 11), 232 ([M]$^+$, 16), 204 (12), 188 (35), 174 (73), 161 (100), 151 (37), 124 (43).

Example S

Preparation of Preparatory Compound S

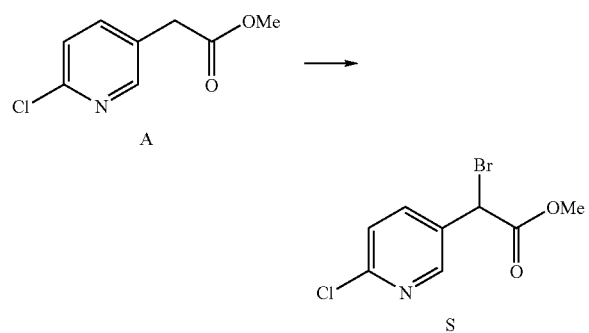

A mixture of 0.500 g (2.69 mmol) of Preparatory Compound A and 479 mg (2.69 mmol) of N-bromosuccinimide in 5 mL of carbon tetrachloride was treated with 5 mg of azobis-isobutyronitrile and was heated at reflux for four hours and was allowed to cool. The mixture was concentrated to dryness and the residue was chromatographed on silica gel (230-400 mesh) using 95/5 dichloromethane/ethyl acetate as eluent to afford 353 mg (50%) of Preparatory Compound S methyl bromo(6-chloro-3-pyridinyl)acetate as an oil; $^1$HNMR (CDCl$_3$) δ 8.44 (d, 1H, J=2.6 Hz), 7.98 (dd, 1H, J=8.3 Hz and J=2.5 Hz), 7.38 (d, 1H, J=8.5 Hz), 5.33 (s, 1H), 3.82 (s, 3H); MS (ES+) m/z 265 ([M+H]$^+$).

Example T

Preparation of Preparatory Compound T

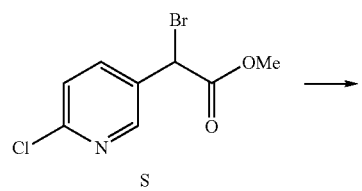

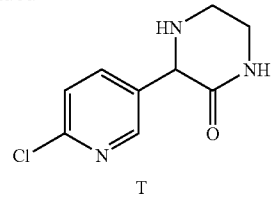

To a solution at 15-20° C. of 8.4 mL (7.55 g, 0.126 mol) of ethylenediamine in 15 mL of dry tetrahydrofuran was added dropwise over a five minute period a solution of 3.2 g (0.012 mol) of Preparatory Compound S in 35 mL of tetrahydrofuran. The mixture was stirred mechanically for 18 h and was then treated with 2.0 g of potassium carbonate and was stirred for four hours. The contents were filtered, the filtrate was concentrated to dryness, and the solid residue was dissolved in 400 mL of dichloromethane and was washed with 20 mL of 10% aqueous potassium carbonate and was then dried over potassium carbonate. Concentration gave 2.61 g of a tan solid. A portion (250 mg) was chromatographed on silica gel (230-400 mesh) using 9/1 dichloromethane/methanol containing 5% ammonium hydroxide to afford 186 mg of Preparatory Compound T 3-(6-chloro-3-pyridinyl)-2-piperazinone as a white solid, mp 157-9° C.; $^1$HNMR (CDCl$_3$) δ 8.50 (d, 1H, J=2.7 Hz), 7.90 (dd, 1H, J=8.4 Hz, and J=2.5 Hz), 7.31 (d, 1H, J=8.2 Hz), 6.37 (br s, 1H), 4.59 (s, 1H), 3.53-3.61 (m, 1H), 3.35-3.40 (m, 1H), 3.08-3.18 (m, 2H), 2.01 (br s, 1H); MS (EI-DIP) m/z 213 ([M+2]$^+$, 7), 211 (M$^+$, 25), 154 (100).

Example U

Preparation of Preparatory Compound U

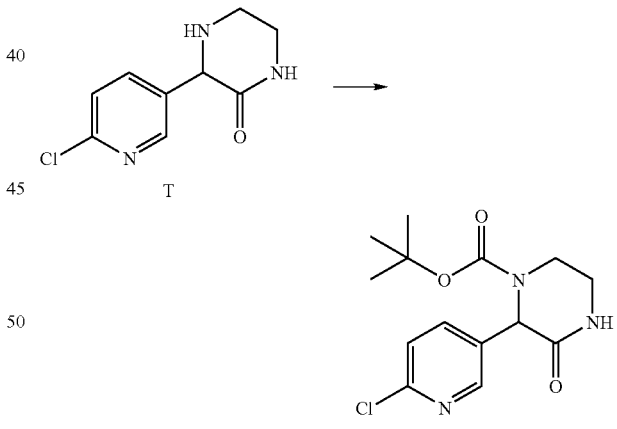

To a solution at 10-20° C. of 2.11 g (9.67 mmol) of di-t-butyldicarbonate in 35 mL of dry tetrahydrofuran was added in portions over a ten minute period 2.00 g (9.45 mmol) of Preparatory Compound T. After stirring at room temperature for 18 h the tetrahydrofuran was removed in vacuo at room temperature and the residue was dissolved in dichloromethane and was washed once with water. The aqueous wash was treated with saturated sodium bicarbonate and was extracted once with dichloromethane. The combined organics were dried over magnesium sulfate and were concentrated to give 2.95 g of Preparatory Compound U tert-butyl 2-(6- chloro-3-pyridinyl)-3-oxo-1-piperazinecarboxylate as a light yellow solid. A portion was recrystallized from ethyl acetate to give mp 168-70° C.; $^1$HNMR (CDCl$_3$) δ 8.44 (d, 1H, J=2.7 Hz), 7.78 (br d, 1H), 7.33 (d, 1H, J=8.5 Hz), 6.54 (br s, 1H), 5.70 (br s, 1H), 4.13 (m, 1H), 3.53-3.57 (m, 1H), 3.31-3.39 (m, 1H), 3.19-3.28 (m, 1H), 1.45 (s, 9H); MS (ES+) m/z 312 ([M+H]$^+$).

Example V

Preparation of Preparatory Compound V

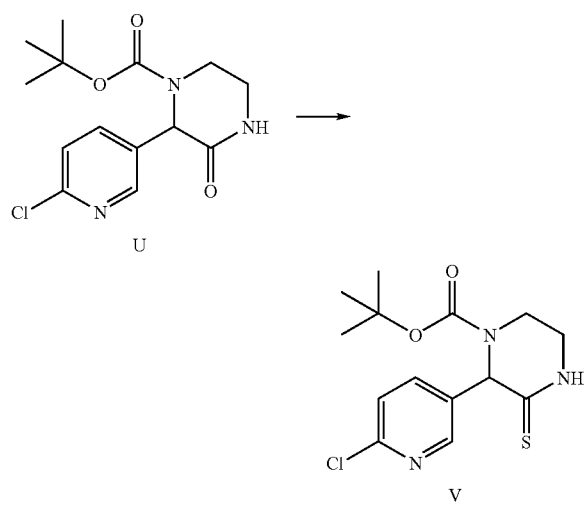

A solution of 312 mg (1.00 mmol) of Preparatory Compound U and 222 mg (1.00 mmol) of phosphorus pentasulfide in 4 mL of dry pyridine was heated at 80° C. for four hours and was allowed to cool. The contents were added dropwise to 30 mL of cold water. Upon warming to room temperature over an hour a fine tan precipitate was present. The mixture was cooled again in ice and the precipitate was collected and air-dried to give 152 mg (46%) of Preparatory Compound V tert-butyl 2-(6-chloro-3-pyridinyl)-3-thioxo-1-piperazinecarboxylate; $^1$HNMR (CDCl$_3$) δ 8.51 (br s and d, 2H, J=2.6 Hz), 7.78 (br d, 1H), 7.33 (d, 1H, J=8.2 Hz), 6.17 (br s, 1H), 4.13 (m, 1H), 3.57 (m, 1H), 3.35-3.48 (m, 1H), 3.23-3.27 (m, 1H), 1.47 (s, 9H); MS (ES+) m/z 328 ([M+H]$^+$).

Example W

Preparation of Preparatory Compound W

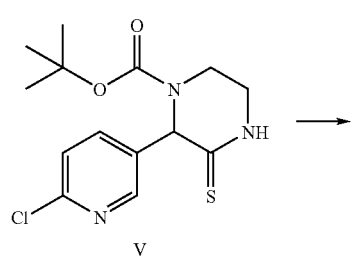

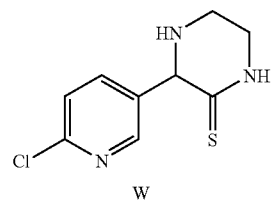

A solution of 970 mg (2.96 mmol) of Preparatory Compound V and 3 mL of trifluoroacetic acid in 15 mL of dichloromethane was stirred at room temperature for three hours. The solution was concentrated in vacuo and the residue was dissolved in dichloromethane and was added to 20 mL of 15% aqueous potassium carbonate. The aqueous phase was then extracted once with dichloromethane and the combined organics were dried over potassium carbonate. Concentration gave 670 mg which was chromatographed on silica gel (230-400 mesh) using 9/1 dichloromethane/methanol containing 5% ammonium hydroxide to afford 260 mg of Preparatory Compound W 3-(6-chloro-3-pyridinyl)-2-piperazinethione; $^1$HNMR (CDCl$_3$) δ 8.54 (br s, 1H), 8.48 (d, 1H, J=2.4 Hz), 7.90 (dd, 1H, J=8.3 Hz, and J=2.6 Hz), 7.32 (d, 1H, J=8.2 Hz), 4.92 (s, 1H), 3.51-3.58 (m, 1H), 3.40-3.48 (m, 1H), 3.15-3.20 (m, 2H), 2.07 (br s, 1H); MS (ES+) m/z 228 ([M+H]$^+$).

Example 1

Preparation of Compound 1

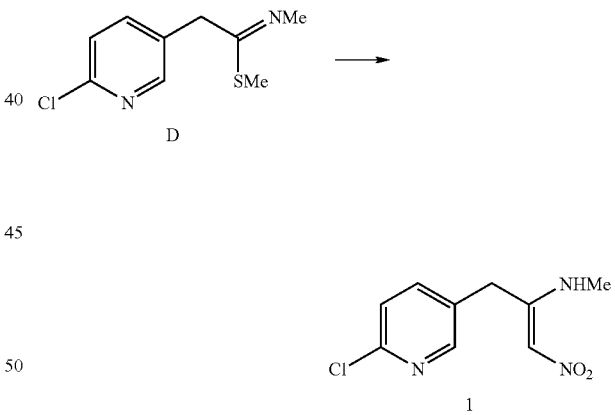

The oily residue containing Preparatory Compound D from Example D was dissolved in 6 mL of nitromethane (pre-treated with neutral alumina and filtered through a membrane) and heated at 100° C. for 24 hours. The clear orange solution was then partitioned between water and ether and the organic layer dried over sodium sulfate. The solvent was removed under reduced pressure and the brown residue purified further by column chromatography on silica gel using 80% ethyl acetate/petroleum ether as the eluent. The solvent was removed under reduced pressure to yield 110 mg (26% over 2 steps) of Compound 1, (1Z)-3-(6-chloro-3-pyridinyl)-N-methyl-1-nitro-1-propen-2-amine, as a light yellow brown solid: mp 124-125° C.; $^1$H NMR (CDCl$_3$) δ 8.32 (d, J=2.6 Hz, 1H), 7.54 (dd, J=2.6 and 7.8 Hz, 1H), 7.36 (d, J=7.6 Hz, 1H), 6.50 (s, 1H), 3.60 (s, 2H), 3.02 (d, J=5.6 Hz, 3H) ppm. MS: (ES−) m/z=226 (M−1).

Example 1A

Alternative Preparation of Compound 1

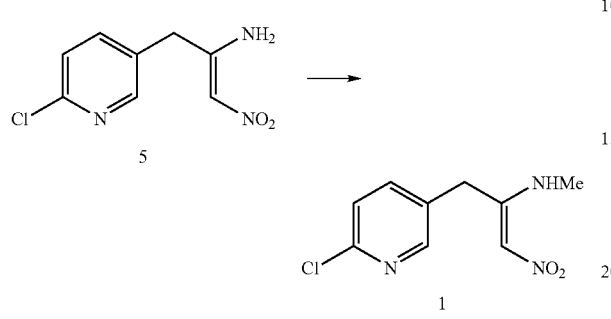

A solution of 240 mg (1.12 mmol) of Compound 5 in 12 mL of 2.0 M methylamine in tetrahydrofuran was stirred at room temperature (about 22° C.) overnight. The solution was concentrated to an oil which was chromatographed on silica gel (230-400 mesh) using 95/5 dichloromethane/methanol as eluent to afford 248 mg (97%) of Compound 1.

Example 2

Preparation of Compound 2

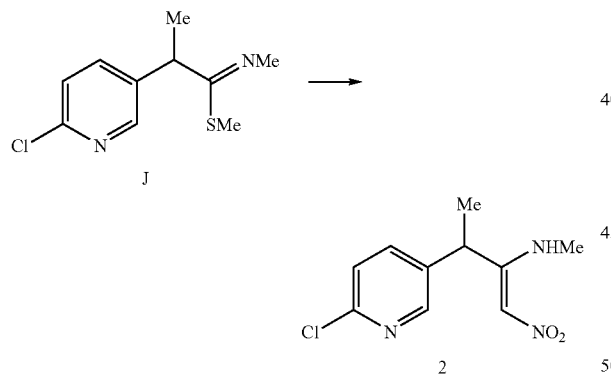

The oily residue containing Preparatory Compound J from Example J was dissolved in 4 mL of a 10:1 mixture of nitromethane and dimethylsulfoxide (pre-treated with neutral alumina and filtered through a membrane) and heated at 115° C. for 36 hours. The clear orange solution was then partitioned between water and ether and the organic layer dried over sodium sulfate. The solvent was removed under reduced pressure and the brown residue purified further by column chromatography on silica gel using 50% ethyl acetate/petroleum ether as the eluent. The solvent was removed under reduced pressure to yield 22 mg (11% over 2 steps) of Compound 2, (1Z)-3-(6-chloro-3-pyridinyl)-N-methyl-1-nitro-1-buten-2-amine, as a light yellow solid: mp 144-145° C.; $^1$H NMR (CDCl$_3$) δ 8.34 (d, J=2.6 Hz, 1H), 7.55 (dd, J=2.6 and 7.8 Hz, 1H), 7.36 (d, J=7.6 Hz, 1H), 6.65 (s, 1H), 4.00 (q, J=7.6 Hz, 1H), 2.98 (d, J=5.7 Hz, 3H), 1.52 (d, J=7.6 Hz, 3H) ppm. MS: (EI-DIP) m/z 241 (M+).

Example 2A

Alternative Preparation of Compound 2

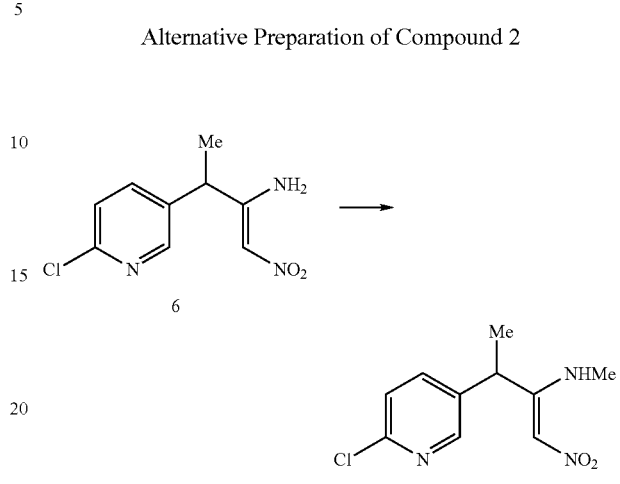

A solution of 610 mg (2.68 mmol) of Compound 6 in 20 mL of 2.0 M methylamine in tetrahydrofuran was heated at 40° C. for 40 hours, was concentrated to a residue and was dissolved in dichloromethane and dried over magnesium sulfate. Concentration gave 720 mg of an oil which was chromatographed on silica gel (230-400 mesh) using 95/5 dichloromethane/methanol as eluent to afford 472 mg (73%) of Compound 2.

Example 3

Preparation of Compound 3

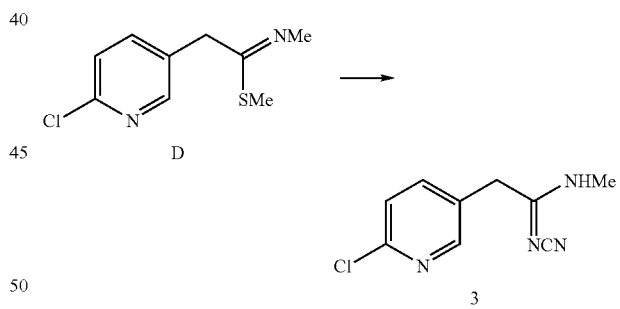

Preparatory Compound D was generated as described above from 580 mg (3.15 mmol) of Preparatory Compound C and 142 mg (3.55 mmol) of 60% sodium hydride. The resulting oily residue was dissolved in 15 mL of dry ethanol and treated with 540 mg (12.9 mmol) of cyanamide under a nitrogen atmosphere. After stirring for 30 minutes at room temperature (about 22° C.), thin layer chromatography and reverse-phase HPLC indicated the reaction was complete. The solvent was removed under reduced pressure, the residue dissolved in dichloromethane and dried over sodium sulfate. The solvent was removed under reduced pressure again and the residue purified further by column chromatography on silica gel using 80% ethyl acetate/petroleum ether as the eluent. The solvent was removed under reduced pressure to yield 385 mg (60% over 2 steps) of Compound 3, (1Z)-2-(6- chloro-3-pyridinyl)-/- cyano-N-methylethanimidamide, as a pale yellow solid: mp 136-138° C.; $^1$H NMR (CDCl$_3$) δ 8.32 (d, J=2.6 Hz, 1H), 7.68 (dd, J=2.6 and 7.8 Hz, 1H), 7.38 (d, J=7.6 Hz, 1H), 3.96 (s, 2H), 2.90 (d, J=5.1 Hz, 3H) ppm. MS: (EI-DIP) m/z 207 (M+). Anal. Calcd for C$_9$H$_9$ClN$_4$: C, 51.8; H, 4.35; N, 26.9. Found: C, 51.9; H, 4.35; N, 26.8.

Example 4

Preparation of Compound 4

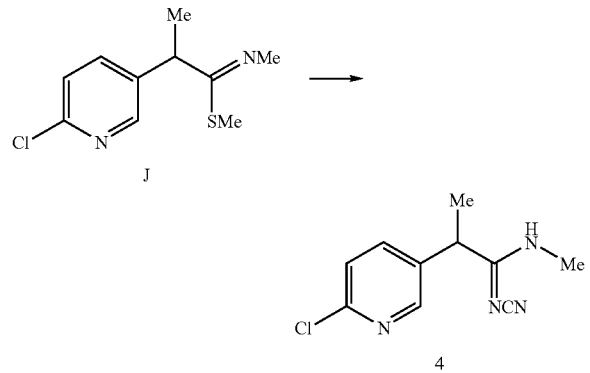

Cyanamide (0.330 g, 0.00789 mol) was added to a solution of Compound J (0.450 g, 0.00197 mol) in 10 mL absolute ethanol under a nitrogen atmosphere. The mixture was heated at 78° C. for 0.5 hours, then concentrated in vacuo. The residue was dissolved in dichloromethane and refrigerated for 16 hours, during which time a precipitate formed. The precipitate was removed by vacuum filtration. The filtrate was dried over magnesium sulfate and concentrated to a yellow oil. The oil was recrystallized in boiling ethyl acetate to yield 0.177 g (40%) of Compound 4, (1Z)-2-(6-chloro-3-pyridinyl)-N-cyano-N-methylpropanimidamide, as a yellow solid. m.p. 170.5-173° C. $^1$H NMR (DMSO-d$_6$) δ 8.73 (br s), 83.8 (d, 1H, J=2.6 Hz), 7.79 (dd, 1H, J=2.7 Hz and 8.6 Hz), 7.54 (d, 1H, J=8.5 Hz), 4.28 (q, 1H, J=7.2 Hz), 2.76 (s, 3H), 1.58 (d, 3H, J=7.3 Hz). MS (ESI) m/z 225 ([M+H]$^+$+2, 37), 223 ([M+H]$^+$, 100), 196 (30).

Example 5

Preparation of Compound 5

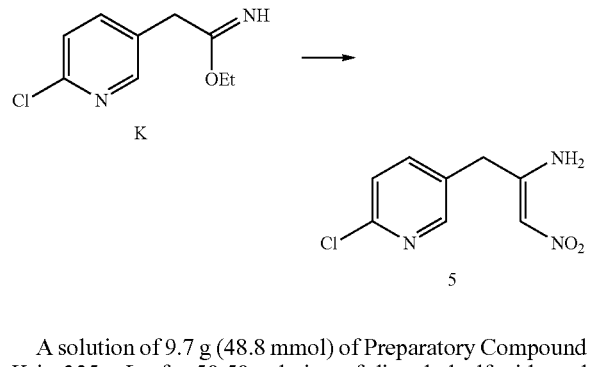

A solution of 9.7 g (48.8 mmol) of Preparatory Compound K in 325 mL of a 50:50 solution of dimethylsulfoxide and nitromethane was heated at 115° overnight. After 17 hours nitromethane and other volatiles were removed in vacuo and the solution was then added dropwise to 1 L of ice water and was then extracted six times with 450 mL of ethyl ether. The combined extracts were dried over magnesium sulfate while the aqueous phase was continuously extracted with ether overnight which was then dried over magnesium sulfate. Concentration of both dried extracts afforded 10.95 g which was triturated under dichloromethane overnight. The mixture was cooled in ice and was filtered to afford 3.2 g (31%) of Compound 5, (1Z)-3-(6-chloro-3-pyridinyl)-1-nitro-1-propen-2-amine. The filtrate was concentrated to give 7.0 g which was chromatographed on silica gel (230-400 mesh) to afford an additional 990 mg of Compound 5.

Example 6

Preparation of Compound 6

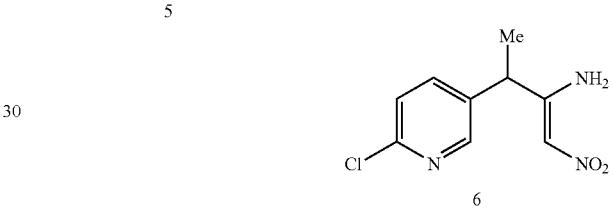

To a mixture of 611 mg (2.86 mmol) of Compound 5 in 4 mL of dry tetrahydrofuran cooled in a dry ice/isopropanol bath was added dropwise via syringe 5.7 mL (5.7 mmol) of a 1.0 M solution of lithium bis(trimethylsilyl)amide in tetrahydrofuran. The contents were stirred at the bath temperature (about −78° C.) for 3 hours and were then treated dropwise with 0.7 mL (11.2 mmol) of methyl iodide over a ten minute period. The mixture was then allowed to warm to room temperature (about 22° C.) overnight. The mixture was cooled in ice and was treated with 5 mL of saturated ammonium chloride was extracted twice with dichloromethane, and the combined extracts were dried with magnesium sulfate. Concentration gave 602 mg of a residue which was chromatographed on silica gel (230-400 mesh) using 96/4 dichloromethane/methanol as eluent to afford 309 mg (47%) of Compound 6, (1Z)-3-(6-chloro-3-pyridinyl)-1-nitro-1-buten-2-amine, mp 83-85° C.

Example 7

Preparation of Compound 7

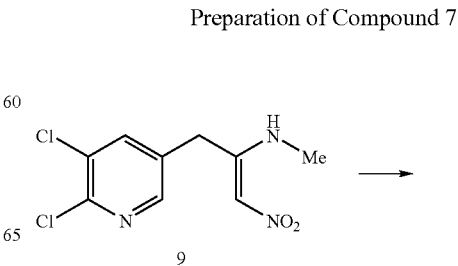

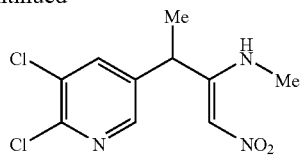

7

Compound 9 (0.26 g, 0.001 mol) was dissolved in anhydrous tetrahydrofuran (7 mL) and cooled to −78° C. N-butyllithium (2.5 M in hexanes, 0.8 mL, 0.002 mol) was added dropwise to the solution. The resulting mixture was stirred for 30 minutes. at −78° C., then iodomethane (0.91 g, 0.0064 mol) was added dropwise to the solution. The mixture was allowed to slowly warm to room temperature (about 22° C.) and stirred overnight. The flask was then cooled to 0° C. Saturated aqueous ammonium chloride was added. The mixture was extracted three times with dichloromethane, and the combined extracts were dried over magnesium sulfate. The solution was concentrated in vacuo, and the residue was purified by column chromatography using 55% hexanes/ethyl acetate as eluents. Fractions containing the desired product were collected and concentrated in vacuo to afford 0.0155 g (5%) of the Compound 7, (N-{(Z)-1-[1-(5,6-dichloropyridin-3-yl)ethyl]-2-nitrovinyl}-N-methylamine), as a yellow solid m.p. 122-123° C. $^1$H NMR δ 8.23 (d, 1H, J=2.1 Hz), 7.66 (d, 1H, J=2.3 Hz), 4.01 (q, 1H, J=7.2 Hz), 2.99 (d, 3H, J=5.6 Hz), 1.53 (d, 3H, J=7.1 Hz). MS (ESI) m/z 278 ([M−H+4]$^+$, 14), 276 ([M−H+2]$^+$, 59), 274 ([M−H]$^+$, 100) 215 (75), 176 (30).

Example 8

Preparation of Compound 8

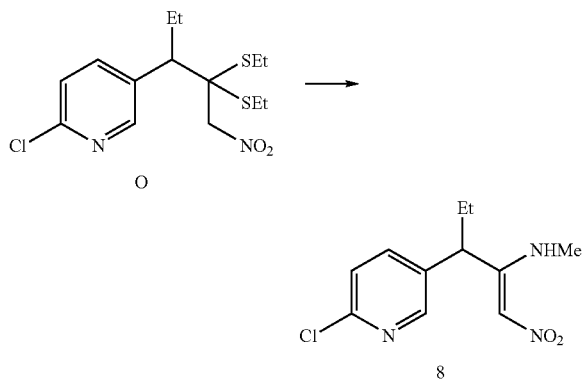

The yellow syrup from Example O containing Preparatory Compound O was dissolved in 10 mL of isopropanol and treated with 5 mL of 1.0M methylamine in tetrahydrofuran. The mixture was heated at 50° C. for 20 minutes. The solvent was removed under reduced pressure and the residue purified by column chromatography on silica gel using 50-80% ethyl acetate/petroleum ether as the eluent. After the solvent was removed under reduced pressure, the residue was dissolved in acetonitrile and passed through a membrane filter to remove the resulting solids. The solvent was removed under reduced pressure to yield 65 mg (10% over 2 steps) of Compound 8, (1Z)-3-(6-chloro-3-pyridinyl)-N-methyl-1-nitro-1-penten-2-amine, as a light yellow solid: mp 93-94° C.; $^1$H NMR (CDCl$_3$) δ 10.3 (bs, 1H), 8.30 (d, J=2.5 Hz, 1H), 7.58 (dd, J=2.5 and 7.5 Hz, 1H), 7.35 (d, J=7.5 Hz, 1H), 6.74 (s. 1H) 3.65 (t, J=7.9 Hz, 1H), 3.00 (d, J=5.9 Hz, 3H), 2.16 (m, 1H), 1.80 (m, 1H) 1.00 (t, J=7.9 Hz, 3H) ppm. MS: (ES−) m/z 254 (M−1).

Example 9

Preparation of Compound 9

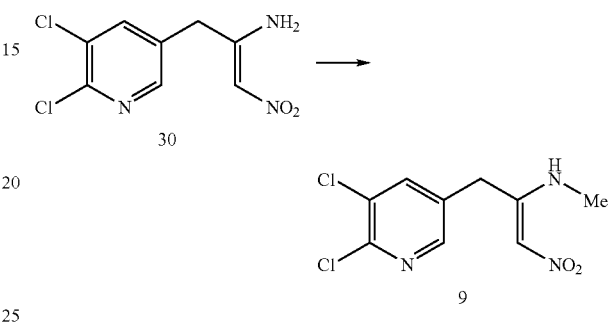

A solution of 2 M methylamine in tetrahydrofuran (7 mL, 0.014 mol) was added to a flask containing Compound 30 (0.231 g, 0.00093 mol). The flask was capped and stirred at room temperature (about 22° C.) overnight. The resulting mixture was concentrated in vacuo to yield Compound 9, N-{(Z)-1-[(5,6-dichloropyridin-3-yl)methyl]-2-nitrovinyl}-N-methylamine, as a dark yellow oil (0.260 g). $^1$H NMR δ 8.24 (d, 1H, J=2.3 Hz), 7.72 (d, 1H, J=2.3 Hz), 6.51 (s, 1H), 3.67 (s, 2H), 3.05 (d, 3H, J=5.0 Hz).

Example 10

Preparation of Compound 10

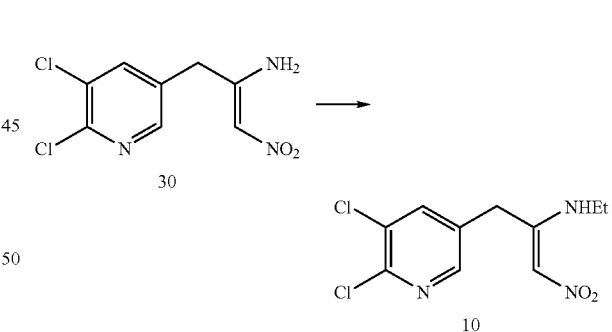

Ethylamine (2.0 M in tetrahydrofuran, 9.2 mL, 0.0184 mol) was added to a flask containing Compound 30 (0.299 g, 0.00121 mol) under nitrogen. The mixture was stirred at room temperature (about 22° C.) overnight. The mixture was concentrated in vacuo and the residue was dissolved in ethyl acetate. The solution was washed with brine and dried over magnesium sulfate, then concentrated in vacuo. The residue was purified by column chromatography using 5% methanol/dichloromethane as eluents. Fractions containing the desired product were collected and concentrated in vacuo to afford 0.276 g (83%) of Compound 10, N-{(Z)-1-[(5,6-dichloropyridin-3-yl)methyl]-2-nitrovinyl}-N-ethylamine, a light orange solid. m.p. 126.5-128° C. $^1$H NMR δ 9.95 (br s, 1H), 8.21 (d, 1H, J=2.3 Hz), 7.66 (d, 1H, J=2.3 Hz), 6.48 (s, 1H), 3.60 (s, 2H), 3.33 (q, 2H, J=6.9 Hz), 1.28 (t, 3H, J=7.3 Hz). MS (ESI) m/z 280 ([M+H+4]$^+$, 10), 278 ([M+H+2]$^+$, 65), 276 ([M+H]$^+$, 100), 217 (29), 215 (46). Anal. Calcd. for $C_{10}H_{11}Cl_2N_3O_2$: C, 43.50; H, 4.02; N, 15.22. Found: C, 43.77; H, 4.02; N, 14.94.

Example 11

Preparation of Compound 11

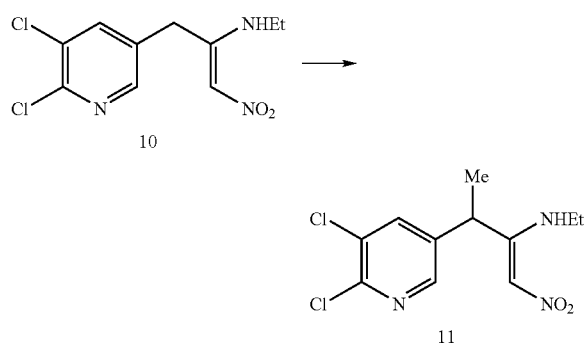

A round-bottomed flask charged with Compound 10 (0.202 g, 0.00073 mol) in tetrahydrofuran (5 mL) was cooled to −78° C. Lithium bis(trimethylsilyl)amide (1.0 M in tetrahydrofuran, 1.6 mL., 0.0016 mol) was added dropwise to the mixture, which was then stirred at −78° C. for 30 minutes. Iodomethane (4.56 g, 0.03213 mol) was added dropwise. The mixture was allowed to slowly warm to room temperature (about 22° C.) and stirred overnight. The mixture was then cooled to 0° C. and treated with saturated aqueous ammonium chloride solution (8 mL). The solution was extracted two times with dichloromethane. The extracts were combined and dried over magnesium sulfate and concentrated in vacuo. The residue was purified by column chromatography using 3% methanol/dichloromethane as eluents. Fractions containing the desired product were combined and concentrated in vacuo to afford an orange oil. The oil was triturated under diethyl ether to yield 0.109 g (52%) of Compound 11, N-{(Z)-1-[1-(5,6-dichloropyridin-3-yl)ethyl]-2-nitrovinyl}-N-ethylamine, as a yellow-orange solid. $^1$H NMR δ 10.15 (br s, 1H), 8.22 (d, 1H, J=2.3 Hz), 7.65 (d, 1H, J=2.3 Hz), 6.60 (s, 1H), 3.99 (q, 1H, J=7.1 Hz), 3.31 (m, 2H), 1.53 (d, 3H, J=7.1 Hz), 1.28 (t, 3H, J=7.2 Hz).

Example 12

Preparation of Compound 12

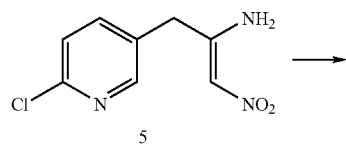

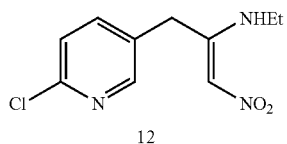

Ethylamine (2.0 M in tetrahydrofuran, 18 mL, 0.036 mol) was added to a flask containing Compound 5 (0.499 g, 0.00235 mol) under nitrogen. The mixture was stirred at room temperature (about 22° C.) overnight. The mixture was then concentrated in vacuo. The residue was triturated under dichloromethane and concentrated again. The residue was purified by column chromatography using 3% methanol/dichloromethane as eluents. Fractions containing Compound 12 were combined and concentrated in vacuo to afford an orange oil. The oil was triturated under diethyl ether to yield 0.53 g (94%) of Compound 12, N-{(Z)-1-[(6-chloropyridin-3-yl)methyl]-2-nitrovinyl}-N-ethylamine. $^1$H NMR δ 9.97 (br s, 1H), 8.29 (dd, 1H, J=0.7 Hz and J=2.6 Hz), 7.53 (dd, 1H, J=2.6 Hz and J=8.2 Hz), 7.36 (d, 1H, J=8.5 Hz), 6.48 (s, 1H), 3.59 (s, 2H), 3.32 (q, 2H, J=7.2 Hz), 1.26 (t, 3H, J=7.3 Hz). MS (ESI) m/z 243 ([M+2]$^+$, 7), 241 ([M]$^+$, 22), 194 (100), 179 (52), 126 (50).

Example 13

Preparation of Compound 13

Propylamine (1.09 g, 0.0185 mol) was added to a flask containing Compound 30 (0.312 g, 0.00126 mol) in tetrahydrofuran (8 mL) under nitrogen. The mixture was stirred overnight. The solution was then concentrated in vacuo to obtain a dark orange oil. The residue was purified by column chromatography using 3% methanol/dichloromethane as eluents. Fractions containing the desired product were combined and concentrated in vacuo to afford an orange solid. The solid was triturated under diethyl ether to yield 0.197 g (54%) of Compound 13, N-{(Z)-1-[(5,6-dichloropyridin-3-yl)methyl]-2-nitrovinyl}-N-propylamine, as an orange solid. $^1$H NMR δ 10.04 (br s, 1H), 8.20 (d, 1H, J=2.1 Hz), 7.64 (d, 1H, J=2.1 Hz), 6.48 (s, 1H), 3.58 (s, 2H), 3.23 (q, 2H, J=6.6 Hz), 1.71-1.63 (m, 2H), 0.98 (t, 3H, J=7.3 Hz).

Example 14

Preparation of Compound 14

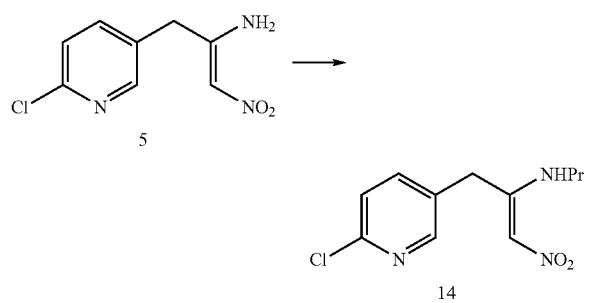

Propylamine (2.12 g, 0.0358 mol) was added to a flask containing Compound 5 (0.500 g, 0.00236 mol) in tetrahydrofuran (15 mL) under nitrogen. The mixture was stirred overnight. The solution was then concentrated in vacuo to obtain a dark brown oil. The residue was purified by column chromatography using 3% methanol/dichloromethane as eluents. Fractions containing the desired product were combined and concentrated in vacuo to yield 0.47 g (78%) of Compound 14, N-{(Z)-1-[(6-chloropyridin-3-yl)methyl]-2-nitrovinyl}-N-propylamine, as an orange solid. $^1$H NMR δ 10.08 (br s, 1H), 8.30 (d, 1H, J=2.4 Hz), 7.53 (dd, 1H, J=2.4 Hz and J=8.6 Hz), 7.36 (d, 1H, J=8.2 Hz), 6.48 (s, 1H), 3.58 (s, 2H), 3.23 (q, 2H, 6.6 Hz), 1.69-1.50 (m, 2H), 0.96 (t, 3H, J=7.4 Hz). MS (ESI) m/z 257 ([M+2]$^+$, 8), 255 ([M]$^+$, 31), 208 (90), 179 (94), 126 (100).

Example 15

Preparation of Compound 15

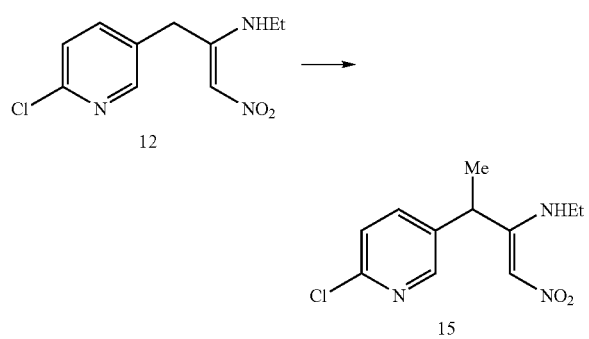

A round-bottomed flask charged with Compound 12 (0.430 g, 0.00178 mol) in tetrahydrofuran (12 mL) was cooled to −78° C. Lithium bis(trimethylsilyl)amide (1.0 M in tetrahydrofuran, 3.8 mL., 0.0038 mol) was added dropwise to the mixture, which was then stirred at −78° C. for 30 minutes. Iodomethane (4.56 g, 0.03213 mol) was added dropwise. The mixture was allowed to slowly warm to room temperature and stirred overnight. The mixture was then cooled to 0° C. and treated with saturated aqueous ammonium chloride solution (20 mL). The mixture was extracted with dichloromethane. The extract was then washed two times with water and dried over magnesium sulfate. The solution was concentrated in vacuo to a dark brown oil. The oil was purified by column chromatography using 20% ethyl acetate/hexanes as eluents. Fractions containing the desired product were collected and concentrated in vacuo to yield 0.159 g (35%) of Compound 15, N-{(Z)-1-[1-(6-chloropyridin-3-yl)ethyl]-2-nitrovinyl}-N-ethylamine, as an amber oil. $^1$H NMR δ 10.18 (br s, 1H), 8.32 (d, 1H, J=2.6 Hz), 7.55 (dd, 1H, J=2.6 Hz and 8.3 Hz), 7.35 (d, 1H, J=8.3 Hz), 6.63 (s, 1H), 3.98 (q, 1H, J=7.2 Hz), 3.45-3.12 (m, 2H), 1.52 (d, 3H, J=7.1 Hz), 1.25 (t, 3H, J=7.22 Hz). Anal. Calcd. for $C_{11}H_{14}ClN_3O$: C, 51.67; H, 5.52; N, 16.43. Found: C, 51.49; H, 5.44; N, 16.18.

Example 16

Preparation of Compound 16

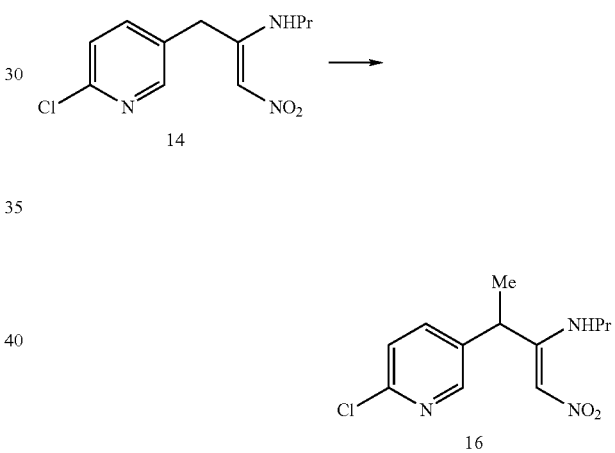

A round-bottomed flask charged with Compound 14 (0.411 g, 0.00162 mol) in tetrahydrofuran (12 mL) was cooled to −78° C. Lithium bis(trimethylsilyl)amide (1.0 M in tetrahydrofuran, 3.5 mL., 0.0035 mol) was added dropwise to the mixture, which was then stirred at −78° C. for 1 hour. Iodomethane (4.56 g, 0.03213 mol) was added dropwise. The mixture was allowed to slowly warm to room temperature and stirred overnight. The mixture was then cooled to 0° C. and treated with saturated aqueous ammonium chloride solution (20 mL). The mixture was extracted with dichloromethane. The extract was then washed two times with water and dried over magnesium sulfate. The solution was concentrated in vacuo to a dark orange oil. The oil was purified by column chromatography using first 15% ethyl acetate/hexanes and then a gradient from 100% dichloromethane to 3% methanol/dichloromethane as eluents. Fractions containing the desired product were collected and concentrated in vacuo to yield 0.090 g (21%) of Compound 16, N-{(Z)-1-[1-(6-chloropyridin-3-yl)ethyl]-2-nitrovinyl)-N-propylamine, as an amber oil. $^1$H NMR δ 10.32 (br s, 1H), 8.32 (d, 1H, J=2.6 Hz), 7.55 (dd, 1H, J=2.6 Hz and J=8.3 Hz), 7.36 (d, 1H, J=8.2 Hz), 6.63

(s, 1H), 3.99 (q, 1H, J=7.2), 3.42-3.06 (m, 2H), 1.68-1.56 (m, 2H), 1.52 (d, 3H, J=7.1 Hz), 0.96 (t, 3H, J=7.39 Hz).

Example 17

Preparation of Compound 17

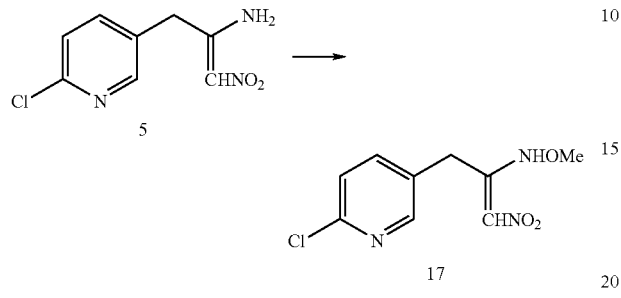

A mixture of 440 mg (2.06 mmol) of Compound 5 and 479 mg (5.73 mmol) of methoxylamine hydrochloride in 3 mL of tetrahydrofuran was treated with 580 mg (5.73 mmol) of triethylamine. The mixture was stirred at room temperature (about 22° C.) for three days and was filtered. The filtrate was concentrated to give 510 mg of a residue which was chromatographed on silica gel using 95/5 dichloromethane/ethyl acetate as eluent to give 356 mg (71%) of Compound 17, 2-chloro-5-[(2Z)-2-(methoxyamino)-3-nitro-2-propenyl]pyridine, as an oil; $^1$H NMR δ (obtained as a mixture of syn and anti isomers, data given for predominant isomer) 3.82 (s, 2H), 4.02 (s, 3H), 4.95 (s, 2H), 7.32 (d, 1H, J=9.0 Hz), 7.47 (dd, 1H, J=8.5 Hz and J=2.5 Hz), 8.24 (d, 1H, J=2.6 Hz); MS (DIP) m/z 245 ([M+2]$^+$, 3), 243 (M$^+$, 10), 166 (100), 126 (97). Anal. Calcd. for $C_9H_{10}ClN_3O_3$: C, 44.36; H, 4.14; N, 17.23. Found: C, 44.29; H, 4.16; N, 17.33.

Example 18

Preparation of Compound 18

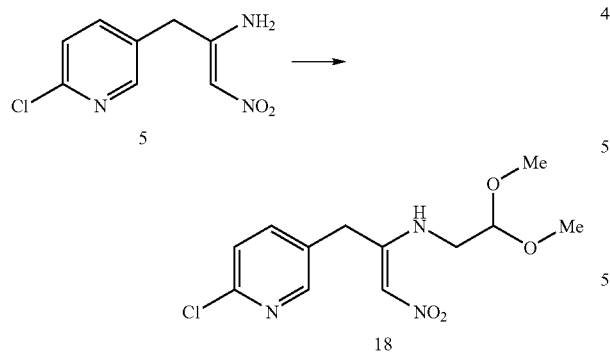

A round-bottomed flask charged with Compound 5 (0.600 g, 0.00283 mol) in tetrahydrofuran (16 mL) was treated with aminoacetaldehyde dimethyl acetal (4.63 g, 0.04406 mol). The flask was capped, and the mixture was stirred at room temperature (about 22° C.) overnight. The solution was concentrated in vacuo and purified by column chromatography using 3% methanol/dichloromethane as eluents. Fractions containing the desired product were collected and concentrated in vacuo to yield 0.658 g (77%) of Compound 18, N-{(Z)-1-[(6-chloropyridin-3-yl)methyl]-2-nitrovinyl}-N-(2,2-dimethoxyethyl)amine, as a greenish oil. $^1$H NMR δ 10.01 (br s, 1H), 8.29, (d, 1H, J=2.6 Hz), 7.53 (dd, 1H, J=2.52 Hz and 8.1 Hz), 7.35 (d, 1H, J=8.2 Hz), 6.46 (s, 1H), 4.38 (t, 1H, J=5.1 Hz), 3.64 (s, 2H), 3.42 (s, 6H), 3.40-3.35 (m, 2H). Anal. Calcd. for $C_{12}H_{16}ClN_3O_4$: C, 47.77; H, 5.34; N, 1.93. Found: C, 47.99; H, 5.32; N, 13.79.

Example 19

Preparation of Compound 19

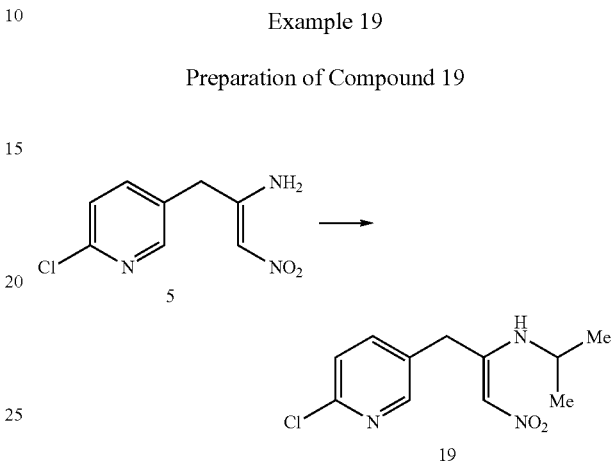

A round-bottomed flask charged with Compound 5 (0.595 g, 0.00280 mol) in tetrahydrofuran (17 mL) was treated with isopropylamine (2.53 g, 0.0429 mol). The flask was capped, and the mixture was stirred at room temperature (about 22° C.) for 72 hours. The solution was concentrated in vacuo and purified by column chromatography using 2% methanol/dichloromethane as eluents. Fractions containing the desired product were collected and concentrated in vacuo to yield 0.427 g (56%) of Compound 19, N-{(Z)-1-[(6-chloropyridin-3-yl)methyl]-2-nitrovinyl}-N-isopropylamine, as a yellow solid. m. p. 89.5-93° C. $^1$H NMR δ 10.03 br s, 1H), 8.30 (d, 1H, J=2.6 Hz), 7.54 (dd, 1H, J=2.3 Hz and J=7.9 Hz), 7.36 (d, 1H, J=8.3 Hz), 6.44 (s, 1H), 3.81-3.73 (m, 1H), 3.59 (s, 2H), 1.23 (d, 6H, J=6.4 Hz). MS (ESI) m/z 258 ([M+2]$^+$, 35), 256 ([M]$^+$, 100), 153 (20).

Example 20

Preparation of Compound 20

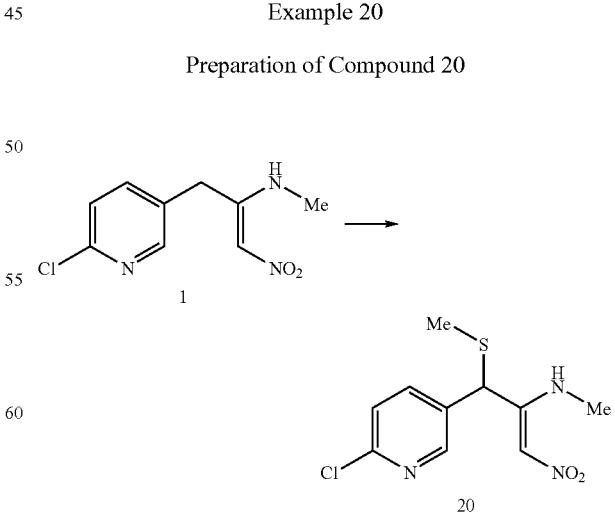

To a solution of Compound 1 (0.227 g, 1.0 mmol) in tetrahydrofuran (10 mL) cooled in a dry ice-acetone bath was added 1.0M lithium bis(trimethylsilyl)amide (2.2 mL, 2.2 mmol) dropwise under nitrogen in 10 minutes and the mixture was stirred for 3 hours. Methyl disulfide liquid (0.45 mL, 5 mmol) was added via a syringe. Dry ice-acetone bath was removed and the temperature was allowed to rise to room temperature (about 22° C.). The reaction was quenched with saturated ammonium chloride aqueous solution, extracted with methylene chloride. The organic phase was washed with water and brine, dried over anhydrous sodium sulfate, concentrated and purified on silica gel column by flash chromatography to give one-spot product. A further purification was carried out on preparative HPLC to give 0.11 g of Compound 20, (1Z)-3-(6-chloro-3-pyridinyl)-N-methyl-3-(methylthio)-1-nitro-1-propen-2-amine, as a light yellow oil in 40% yield.

Example 21

Preparation of Compound 21

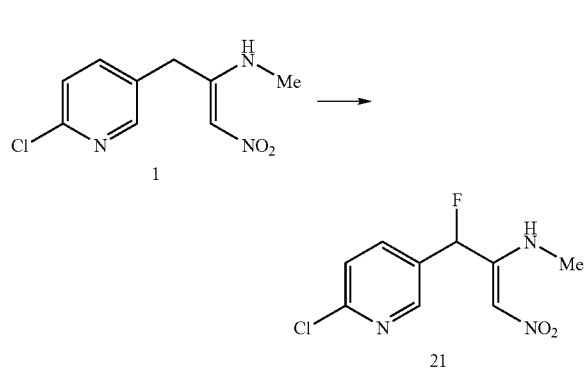

By following the procedure described for Compound 20, 0.227 g of Compound 1 (1.0 mmol) was deprotonated by 1.0 M lithium bis(trimethylsilyl)amide (2.2 mL, 2.2 mmol) and reacted with N-fluorodibenzenesulfonamide (0.30 g, 4 mmol) to give 0.104 g Compound 21, (1Z)-3-(6-chloro-3-pyridinyl)-3-fluoro-N-methyl-1-nitro-1-propen-2-amine, as brownish oil in 42% yield.

Example 22

Preparation of Compound 22

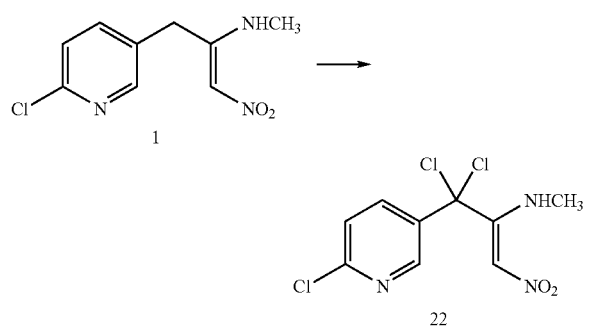

Using the procedure described for Compound 20, the same amount of Compound 1 was reacted with hexachloroethane (0.94 g, 4.0 mmol) to give 0.224 g of Compound 22, (1Z)-3,3-dichloro-3-(6-chloro-3-pyridinyl)-N-methyl-1-nitro-1-propen-2-amine, as a yellowish solid in 76% yield.

Example 23

Preparation of Compound 23

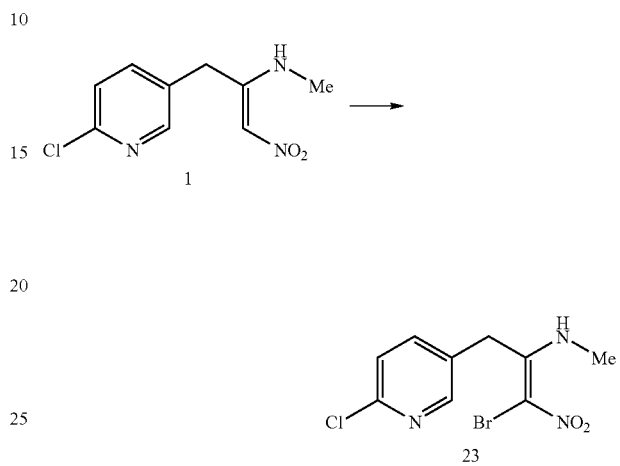

A mixture of Compound 1 (0.113 g, 0.5 mmol), N-bromosucciniamide (0.104 g, 0.6 mmol) and sodium methoxide (0.030 g, 0.55 mmol) in $CCl_4$ (50 mL) was stirred at room temperature (about 22° C.) overnight. The mixture was then washed with water and brine, dried over anhydrous sodium sulfate, purified on silica gel (30% ethylacetate in dichloromethane) to give 0.041 g of Compound 23, (1E)-1-bromo-3-(6-chloro-3-pyridinyl)-N-methyl-1-nitro-1-propen-2-amine, in 27% yield.

Example 24

Preparation of Compound 24

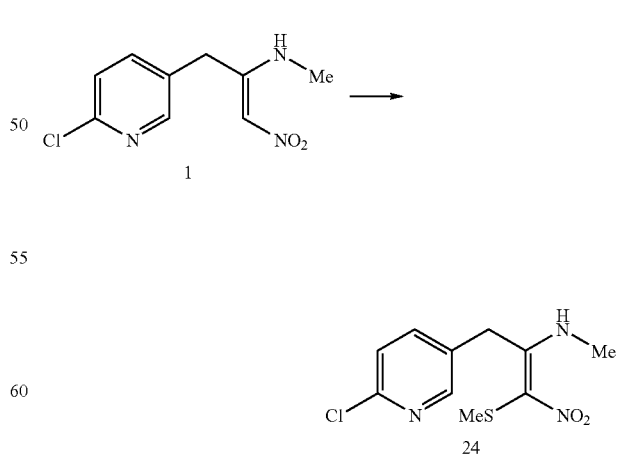

Using the procedure described for Compound 23, the same amount of Compound 1 was reacted with sodium thiomethoxide (0.039 g, 0.55 mmol) to give 0.030 g of Compound 24, (1E)-3-(6-chloro-3-pyridinyl)-N-methyl-1-(methylthio)-1-nitro-1-propen-2-amine, as a yellowish oil in 19% yield.

Example 25

Preparation of Compound 25

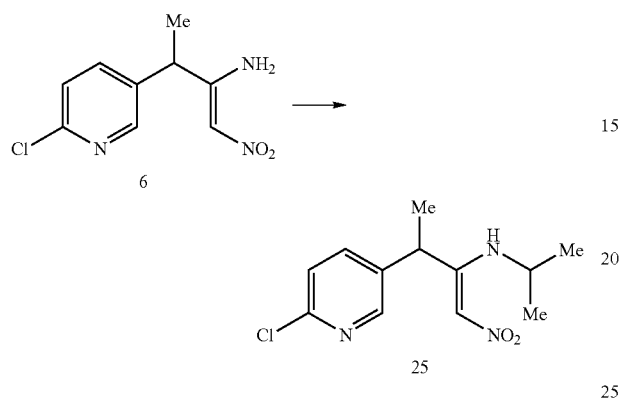

Compound 6 (0.288 g, 0.00133 mol) was dissolved in tetrahydrofuran (9 mL) and isopropylamine (10 mL) and heated at 35° C. for 120 hours. The resulting mixture was cooled and concentrated in vacuo to a yellow oil, which was purified by column chromatography using 25% ethyl acetate/hexanes as eluents. Fractions containing the desired product were collected and concentrated in vacuo to a clear oil, which was triturated under diethyl ether to obtain 0.0699 g (19%) of Compound 25, N-{(Z)-1-[1-(6-chloropyridin-3-yl)ethyl]-2-nitrovinyl}-N-isopropylamine, as an off-white solid. m.p. 116-118° C. $^1$H NMR δ 10.29 (br s, 1H), 8.32 (d, 1H, J=2.6 Hz), 7.54 (dd, 1H, J=2.5 Hz and J=8.3 Hz), 7.35 (d, 1H, J=8.2 Hz), 6.56 (s, 1H), 4.00 (q, 1H, J=7.2 Hz), 3.84-3.76 (m, 1H), 1.54 (d, 3H, J=7.1 Hz), 1.31 (d, 3H, J=6.4 Hz), 1.10 (d, 3H, J=6.3 Hz). MS (ESI) m/z 272 ([M+H+2]$^+$, 38), 270 ([M+H]$^+$, 100), 252 (16), 223 (27), 167 (23). Anal. Calcd. for $C_{12}H_{16}ClN_3O_2$: C, 53.44; H, 5.98; N, 15.58. Found: C, 53.64; H, 6.11; N, 15.24.

Example 26

Preparation of Compound 26

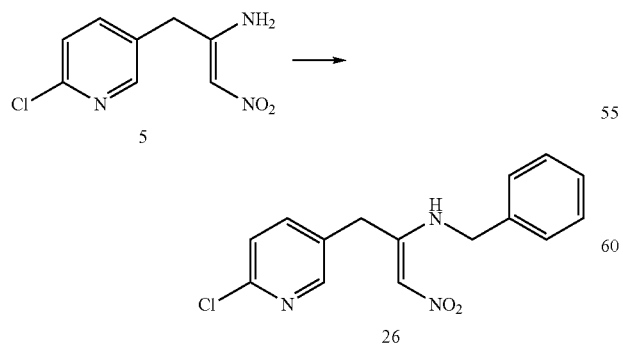

A round-bottomed flask charged with Compound 5 (0.611 g, 0.00288 mol) in tetrahydrofuran (2 mL) was treated with benzylamine (0.352 g, 0.00328 mol). The flask was capped, and the mixture was stirred at room temperature (about 22° C.) overnight. The temperature was then increased to 40° C., and the solution was stirred for an additional 24 hours at this temperature. The flask was cooled to room temperature (about 22° C.). The material was dissolved in dichloromethane and washed with brine. The brine layer was extracted with dichloromethane once, then the combined organic phases were dried over magnesium sulfate. The solution was concentrated in vacuo to give a dark brown solid, which was triturated under cold diethyl ether to yield 0.629 g (72%) of Compound 26, N-benzyl-N-{(Z)-1-[(6-chloropyridin-3-yl)methyl]-2-nitrovinyl}amine, as a tan solid. m.p. 112-114.5° C. $^1$H NMR δ 10.33 (br s, 1H), 8.26 (d, 1H, J=2.4 Hz), 7.49 (dd, 1H, J=2.4 Hz and 8.2 Hz), 7.42-7.26 (m, 5H), 7.18 (d, 1H, J=5.9 Hz), 6.52 (s, 1H), 4.47 (d, 2H, J=6.4 Hz), 3.58 (s, 1H). Anal Calcd. for $C_{15}H_{14}ClN_3O_2$: C, 59.31; H, 4.65; N, 13.83. Found: C, 59.03; H, 4.79; N, 13.64.

Example 27

Preparation of Compound 27

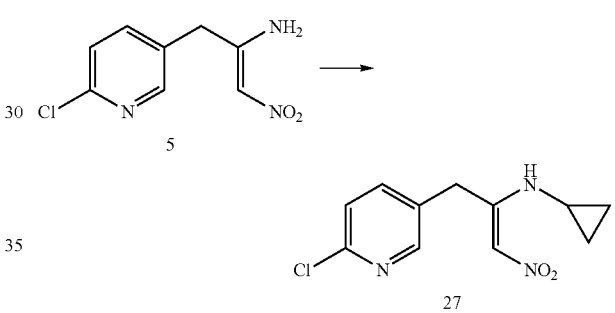

A round-bottomed flask charged with Compound 5 (0.641 g, 0.00302 mol) was treated with cyclopropylamine (2.47 g, 0.04329 mol). The flask was capped, and the mixture was stirred at room temperature (about 22° C.) overnight. The mixture was concentrated in vacuo to give a dark brown oil, which was dissolved in dichloromethane and washed with brine. The brine layer was extracted with dichloromethane once, then the combined organic phases were dried over magnesium sulfate. The solution was concentrated in vacuo to give a dark orange oil, which was purified by column chromatography using 20% ethyl acetate/dichloromethane as eluents. Fractions containing the desired compound were collected and concentrated in vacuo to yield 0.450 g (59%) of Compound 27, N-{(Z)-1-[(6-chloropyridin-3-yl)methyl]-2-nitrovinyl}-N-cyclopropylamine, as a yellow oil.

Example 28

Preparation of Compound 28

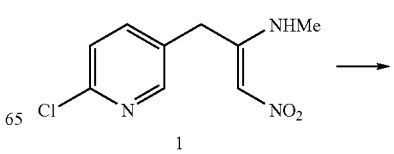

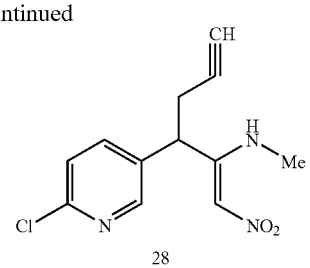

28

By following the procedure described for Compound 20, 0.227 g of Compound 1 (1.0 mmol) was deprotonated by lithium bis(trimethylsilyl)amide (2.2 mL, 2.2 mmol) and then reacted with propargyl bromide (0.65 g, 5.0 mmol) to give 0.065 g of Compound 28, (1Z)-3-(6-chloro-3-pyridinyl)-N-methyl-1-nitro-1-hexen-5-yn-2-amine, as a yellowish foam upon drying under vacuum in a yield of 24%.

Example 29

Preparation of Compound 29

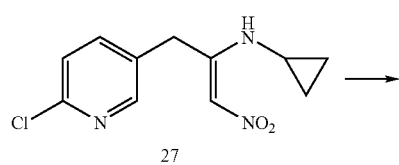

27

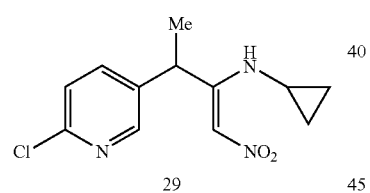

29

A round-bottomed flask charged with Compound 27 (0.380 g, 0.00150 mol) in tetrahydrofuran (10 mL) was cooled to −78° C. Lithium bis(trimethylsilyl)amide (1.0 M in tetrahydrofuran, 3.4 mL., 0.00340 mol) was added dropwise to the mixture, which was then stirred at −78° C. for 2 hours. Iodomethane (4.56 g, 0.03213 mol) was added dropwise. The mixture was allowed to slowly warm to room temperature and stirred overnight. The mixture was then cooled to 0° C. and treated with saturated aqueous ammonium chloride solution (18 mL). The mixture was extracted with dichloromethane. The extract was then washed two times with water and dried over magnesium sulfate. The solution was concentrated in vacuo to a dark orange oil. The oil was purified by column chromatography using 5% ethyl acetate/dichloromethane as eluents. Fractions containing the desired product were collected and concentrated in vacuo to afford a yellow oil, which was triturated under cold ethyl ether to yield 0.035 g (9%) of Compound 29, N-{(Z)-1-[1-(6-chloropyridin-3-yl)ethyl]-2-nitrovinyl}-N-cyclopropylamine, as a yellow powder.

Example 30

Preparation of Compound 30

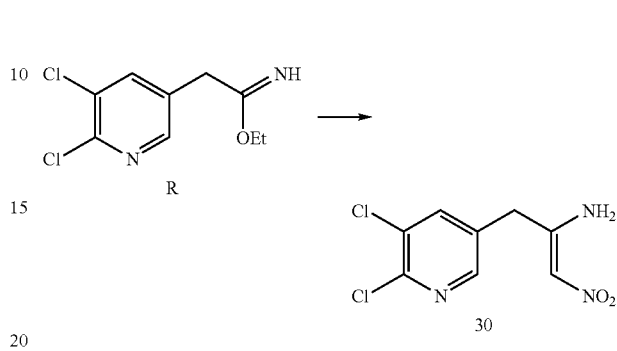

30

Dimethylsulfoxide (23 mL) and nitromethane (23 mL) were combined and dried for 4 hours over alumina. The mixture was filtered into a flask containing Preparatory Compound R (0.93 g, 0.00401 mol). The flask was fitted with a reflux condenser and heated at 115° C. overnight. The mixture was cooled to room temperature (about 22° C.) and concentrated in vacuo. The residue was added dropwise to ice, then extracted four times with 400 mL diethyl ether. The extracts were combined and dried over magnesium sulfate, then concentrated in vacuo. The residue was purified by column chromatography using 20% ethyl acetate/dichloromethane as eluents. Fractions containing the desired product were collected and concentrated in vacuo to afford 0.300 g (30%) of Compound 30, (Z)-1-[(5,6-dichloropyridin-3-yl) methyl]-2-nitrovinylamine, as a yellow solid. $^1$H NMR (DMSO-$d_6$) δ 9.05 (br s, 1H), 8.78 (br s, 1H), 8.42 (d, 1H, J=2.1 Hz), 8.17 (d, 1H, J=2.1 Hz), 6.72 (s, 1H), 3.55 (s, 2H).

Example 31

Preparation of Compound 31

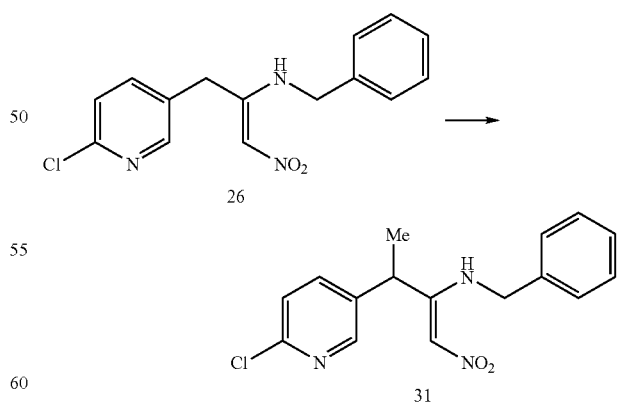

31

A round-bottomed flask charged with Compound 26 (0.545 g, 0.00180 mol) in tetrahydrofuran (10 mL) was cooled to −78° C. Lithium bis(trimethylsilyl)amide (1.0 M in tetrahydrofuran, 4.0 mL., 0.00400 mol) was added dropwise to the mixture, which was then stirred at −78° C. for 2 hours.

Iodomethane (4.56 g, 0.03213 mol) was added dropwise. The mixture was allowed to slowly warm to room temperature and stirred overnight. The mixture was then cooled to 0° C. and treated with saturated aqueous ammonium chloride solution (22 mL). The mixture was extracted with dichloromethane. The extract was then washed two times with water and dried over magnesium sulfate. The solution was concentrated in vacuo to a dark orange oil. The oil was purified by column chromatography using 50% ethyl acetate/hexanes as eluents. Fractions containing the desired product were collected and concentrated in vacuo to afford a yellow oil, which was triturated under ethyl ether to yield 0.175 g (31%) of Compound 31, N-benzyl-N-{(Z)-1-[1-(6-chloropyridin-3-yl)ethyl]-2-nitrovinyl}amine, as a yellow powder. m.p. 77-81° C.

Example 32

Preparation of Compound 32

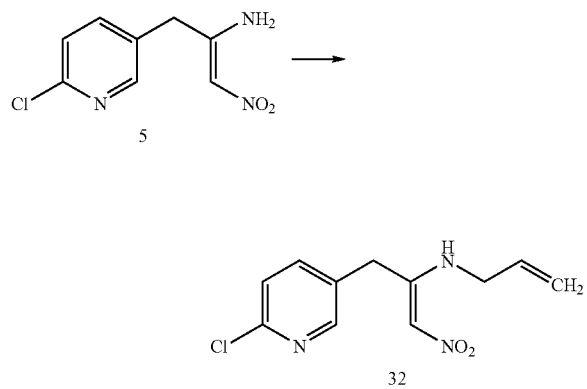

A round-bottomed flask charged with Compound 5 (0.400 g, 0.00187 mol) was dissolved in tetrahydrofuran (10 mL) and treated with allylamine (1.64 g, 0.02880 mol). The flask was capped, and the mixture was stirred at room temperature (about 22° C.) for 3 days. The mixture was concentrated in vacuo to give a dark brown oil. The oil was purified by column chromatography using 30% ethyl acetate/dichloromethane as eluents. Fractions containing the desired product were combined and concentrated in vacuo to obtain a clear oil, which gradually solidified and colored to afford 0.295 mg (62.5%) of Compound 32, N-{(Z)-1-[(6-chloropyridin-3-yl)methyl]-2-nitrovinyl}prop-2-en-1-amine, as a light orange solid. m.p. 84-88.5° C.

Example 33

Preparation of Compound 33

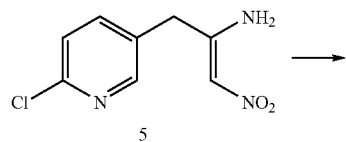

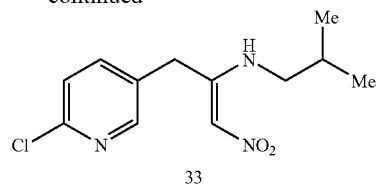

A round-bottomed flask charged with Compound 5 (0.492 g, 0.00232 mol) was treated with isobutylamine (2.47 g, 0.04329 mol). The flask was capped, and the mixture was stirred at room temperature (about 22° C.) overnight. The mixture was concentrated in vacuo to give a dark solid, which was dissolved in dichloromethane and washed with brine. The solution was dried over magnesium sulfate and concentrated in vacuo to afford 0.484 g (78%) of Compound 33, N-{(Z)-1-[(6-chloropyridin-3-yl)methyl]-2-nitrovinyl}-N-isobutylamine, as a tan solid. m.p. 86-92.5° C.

Example 34

Preparation of Compound 34

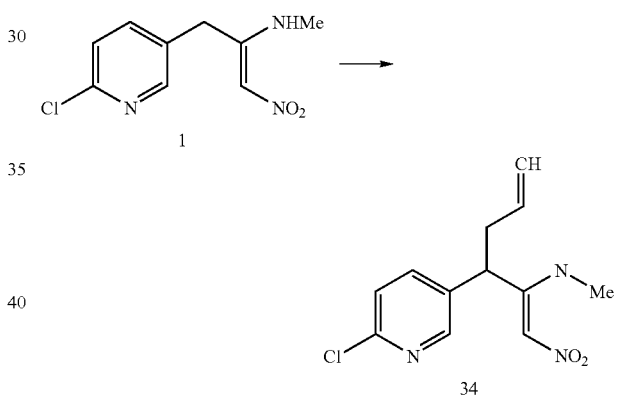

By following the procedure described for Compound 20, 0.227 g of Compound 1 (1.0 mmol) was deprotonated by lithium bis(trimethylsilyl)amide (2.1 mL, 2.1 mmol) and reacted with allyl bromide (0.60 g, 5.0 mmol) to give 0.193 g of Compound 34, (1Z)-3-(6-chloro-3-pyridinyl)-N-methyl-1-nitro-1,5-hexadien-2-amine, as a brownish oil in 72% yield.

Example 35

Preparation of Compound 35

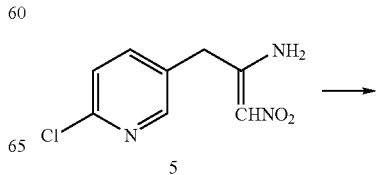

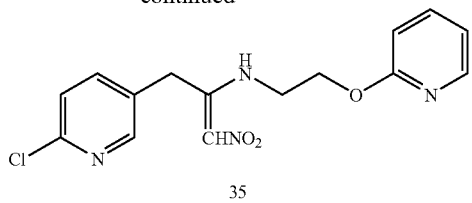

A solution of 1.00 g (4.68 mmol) of Compound 5 and 606 mg (4.39 mmol) of 2-(2-aminoethoxy)pyridine [Tetrahedron, 44, 91 (1988)] in 5 mL of tetrahydrofuran was heated at 40° C. for 32 hours and was allowed to cool. The volatiles were removed in vacuo and the resulting oil was chromatographed on silica gel using 95/5 dichloromethane/methanol as eluent to give 1.1 g (75%) of Compound 35, (1Z)-3-(6-chloro-3-pyridinyl)-1-nitro-N-[2-(2-pyridinyloxy)ethyl]-1-propen-2-amine, as a white solid, mp 112-114.5° C.; $^1$H NMR δ3.63-3.69 (m, 4H), 4.48 (m, 2H), 6.48 (s, 1H), 6.75 (d, 1H, J=8.4 Hz), 6.93 (m, 1H), 7.32 (d, 1H, J=8.4 Hz), 7.51 (dd, 1H, J=8.9 Hz and J=1.8 Hz), 7.61 (m, 1H), 8.15 (m, 1H), 8.27 (d, 1H, J=2.4 Hz), 10.33 (br s, 1H); MS (ESI+) m/z 337 ([M+2+H]$^+$, 42), 335 ([M+H]$^+$, 100.

Example 36

Preparation of Compound 36

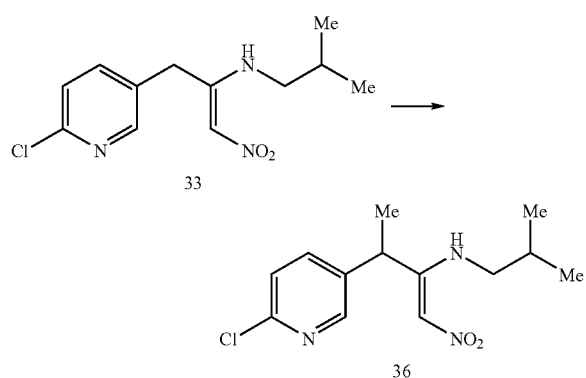

A round-bottomed flask charged with Compound 33 (0.411 g, 0.00153 mol) in tetrahydrofuran (8 mL) was cooled to −78° C. Lithium bis(trimethylsilyl)amide (1.0 M in tetrahydrofuran, 3.4 mL., 0.00340 mol) was added dropwise to the mixture, which was then stirred at −78° C. for 0.5 hours. Iodomethane (4.56 g, 0.03213 mol) was added dropwise. The mixture was allowed to slowly warm to room temperature and stirred overnight. The mixture was then cooled to 0° C. and treated with saturated aqueous ammonium chloride solution (18.5 mL). The mixture was extracted with dichloromethane. The extract was then washed with water and dried over magnesium sulfate. The solution was concentrated in vacuo to a dark orange oil. The oil was purified by column chromatography using a gradient from 100% dichloromethane to 10% ethyl acetate/dichloromethane as eluents. Fractions containing the desired product were collected and concentrated in vacuo to afford an orange oil, which was triturated under ethyl ether to yield 0.244 g (56%) of Compound 36, N-{(Z)-1-[1-(6-chloropyridin-3-yl)ethyl]-2-nitrovinyl}-N-isobutylamine, as a yellow solid. m.p. 87-92° C.

Example 37

Preparation of Compound 37

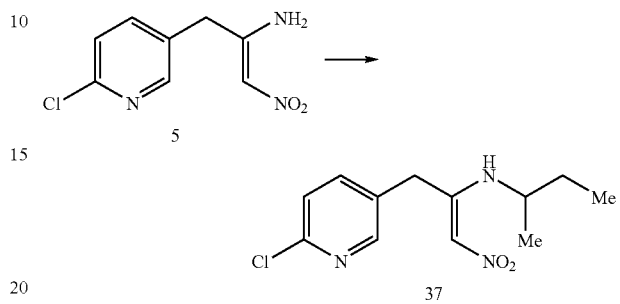

A round-bottomed flask charged with Compound 5 (0.737 g, 0.00348 mol) was treated with sec-butylamine (4.34 g, 0.05939 mol). The flask was capped, and the mixture was stirred at room temperature (about 22° C.) for 36 hours, then heated at 50° C. for an additional 8 hours. The mixture was brought up in dichloromethane, washed with saturated brine solution, and dried over magnesium sulfate. It was then concentrated in vacuo to yield 0.589 g (63%) of Compound 37, N-(sec-butyl)-N-{(Z)-1-[(6-chloropyridin-3-yl)methyl]-2-nitrovinyl}amine, as a copper solid. m.p. 98.5-105.5° C.

Example 38

Preparation of Compound 38

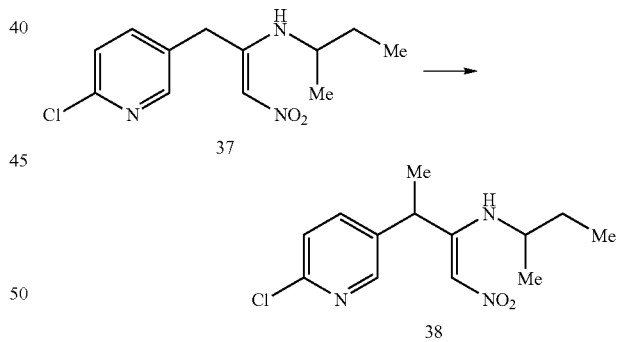

A round-bottomed flask charged with Compound 37 (0.500 g, 0.00186 mol) in tetrahydrofuran (10 mL) was cooled to −78° C. Lithium bis(trimethylsilyl)amide (1.0 M in tetrahydrofuran, 4.0 mL., 0.00400 mol) was added dropwise to the mixture, which was then stirred at −78° C. for 0.5 hours. Iodomethane (4.56 g, 0.03213 mol) was added dropwise. The mixture was allowed to slowly warm to room temperature and stirred overnight. The mixture was then cooled to 0° C. and treated with saturated aqueous ammonium chloride solution (17 mL). The mixture was extracted with dichloromethane. The extract was then washed with water and dried over magnesium sulfate. The solution was concentrated in vacuo to a dark orange oil. The oil was purified by column chromatography using a gradient from 100% dichloromethane to 10% ethyl acetate/dichloromethane as eluents. Fractions containing the desired product were collected and concentrated in vacuo to yield 0.298 g (57%) of Compound 38, N-(sec-butyl)-N-{(Z)-1-[1-(6-chloropyridin-3-yl)ethyl]-2-nitrovinyl}amine, as an orange solid. m.p. 88-92° C.

Example 39

Preparation of Compound 39

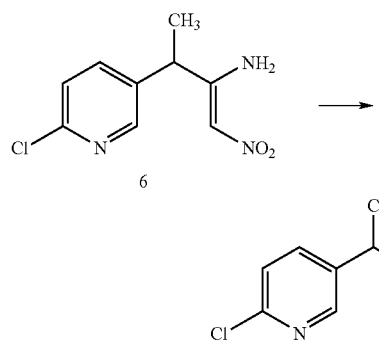

A round-bottomed flask charged with Compound 6 (0.145 g, 0.00064 mol) in tetrahydrofuran (2 mL) was treated with allylamine (1.52 g, 0.00266 mol). The flask was capped, and the mixture was stirred at room temperature (about 22° C.) overnight. The mixture was concentrated in vacuo to afford a yellow oil, which was purified by column chromatography using 10% ethyl acetate/dichloromethane as eluents. Fractions containing the desired compound were combined and concentrated in vacuo to yield 0.074 g (41%) of Compound 39, N-allyl-N-{(Z)-1-[1-(6-chloropyridin-3-yl)ethyl]-2-nitrovinyl}amine, as a yellow oil.

Example 40

Preparation of Compound 40

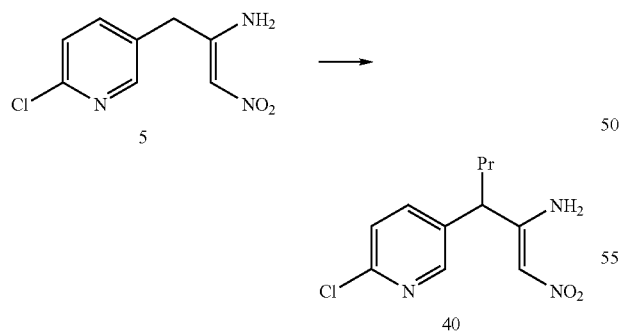

A round-bottomed flask charged with Compound 5 (0.750 g, 0.00354 mol) in tetrahydrofuran (10 mL) was cooled to −78° C. Lithium bis(trimethylsilyl)amide (1.0 M in tetrahydrofuran, 7.7 mL., 0.00770 mol) was added dropwise to the mixture, which was then stirred at −78° C. for 0.5 hours. 1-iodopropane (3.49 g, 0.0205 mol) was added dropwise. The mixture was allowed to slowly warm to room temperature and stirred overnight. The mixture was then cooled to 0° C. and treated with saturated aqueous ammonium chloride solution (32 mL). The mixture was extracted with dichloromethane. The extract was then washed with water and dried over magnesium sulfate. The solution was concentrated in vacuo to a dark brown oil. The oil was purified by column chromatography using 20% ethyl acetate/dichloromethane as eluents. Fractions containing the desired product were collected and concentrated in vacuo to yield 0.230 g (25.5%) of Compound 40, (Z)-1-[1-(6-chloropyridin-3-yl)butyl]-2-nitrovinylamine, as a dark yellow oil.

Example 41

Preparation of Compound 41

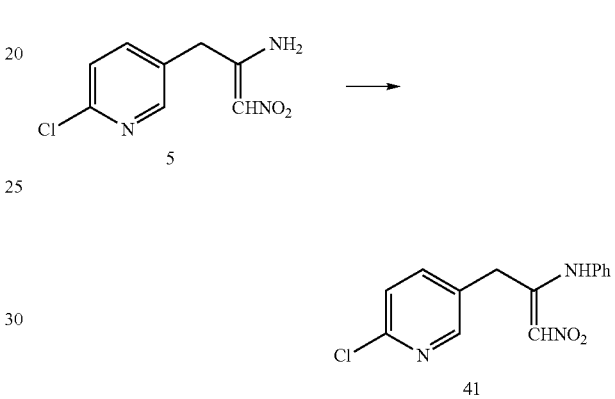

A mixture of 300 mg (1.40 mmol) of Compound 5, 325 mg (1.40 mmol) of camphor sulfonic acid, and 131 mg (1.41 mmol) of aniline in 8 mL of 1,2-dichloroethane was stirred at room temperature (about 22° C.) for 5 days. The contents were diluted with dichloromethane and were washed twice with saturated sodium bicarbonate and were dried (magnesium sulfate). Concentration gave 400 mg which was chromatographed on silica gel using a dichloromethane/methanol gradient as eluent to afford 300 mg (74%) of Compound 41, N-{(Z)-1-[(6-chloro-3-pyridinyl)methyl]-2-nitroethenyl}aniline, as a pale yellow solid, mp 143-145° C.; $^1$H NMR δ 3.57 (s, 2H), 6.62 (s, 1H), 7.06 (m, 2H), 7.23 (d, 1H, J=7.8 Hz), 7.31 (dd, 1H, J=8.4 Hz and J=2.5 Hz), 7.38-7.40 (m, 3H), 7.82 (d, 1H, J=2.1 Hz), 11.3 (br s, 1H); MS (ESI−) m/z 290 ([M+2-H]$^+$, 34), 288 ([M−H]$^+$, 100. Anal. Calcd. for $C_{14}H_{12}ClN_3O_2$: C, 58.03; H, 4.18; N, 14.50. Found: C, 57.86; H, 4.30; N, 14.32.

Example 42

Preparation of Compound 42

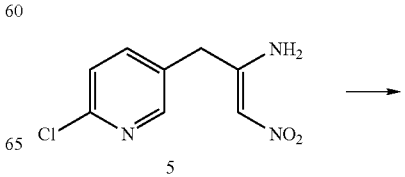

-continued

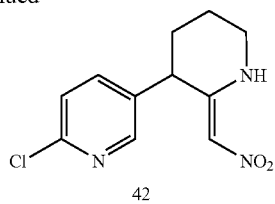
42

A round-bottomed flask charged with Compound 5 (0.749 g, 0.00353 mol) in tetrahydrofuran (15 mL) was cooled to −78° C. Lithium bis(trimethylsilyl)amide (1.0 M in tetrahydrofuran, 8.0 mL., 0.00800 mol) was added dropwise to the mixture, which was then stirred at −78° C. for 0.5 hours. 1,3-dibromopropane (3.98 g, 0.0198 mol) was added dropwise. The mixture was allowed to slowly warm to room temperature and stirred overnight. The mixture was then cooled to 0° C. and treated with saturated aqueous ammonium chloride solution (10 mL). The mixture was extracted with dichloromethane. The extract was then washed with water and dried over magnesium sulfate. The solution was concentrated in vacuo to a dark orange oil. The oil was purified by column chromatography using first 80% ethyl acetate/hexanes, followed by 5% methanol/dichloromethane as eluents. Fractions containing the desired product were collected and concentrated in vacuo to yield 0.186 g (21%) of Compound 42, 2-chloro-5-[(2Z)-2-(nitromethylene)piperidin-3-yl]pyridine, as a yellow solid. m.p. 132.5-134° C.

Example 43

Preparation of Compound 43

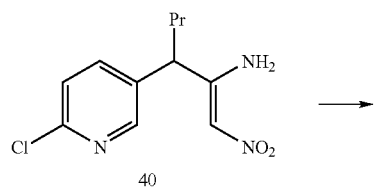

A round-bottomed flask charged with Compound 40 (0.179 g, 0.00070 mol) was treated with methylamine (2.0 M in tetrahydrofuran, 2.0 mL, 0.00400 mol). The flask was capped, and the mixture was stirred at 50° C. overnight. The mixture was cooled to room temperature (about 22° C.) and concentrated in vacuo to afford an orange oil, which was purified by column chromatography using 80% ethyl acetate/hexanes as eluents. Fractions containing the desired compound were combined and concentrated in vacuo to yield 0.117 g (62%) of Compound 43, N-{(Z)-1-[1-(6-chloropyridin-3-yl)butyl]-2-nitrovinyl}-N-methylamine, as a pale yellow oil.

Example 44

Preparation of Compound 44

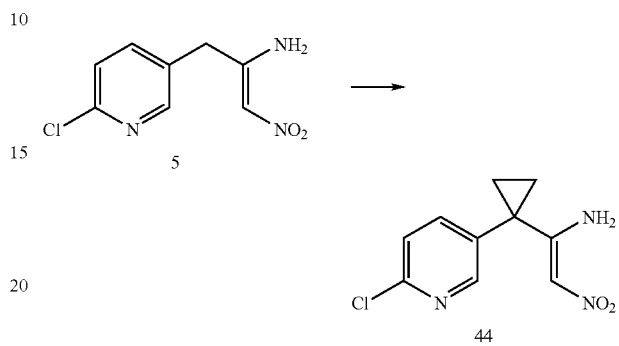

A round-bottomed flask charged with Compound 5 (0.750 g, 0.00354 mol) in tetrahydrofuran (15 mL) was cooled to −78° C. Lithium bis(trimethylsilyl)amide (1.0 M in tetrahydrofuran, 8.0 mL., 0.00800 mol) was added dropwise to the mixture, which was then stirred at −78° C. for 0.5 hours. 1,2-Dibromoethane (3.99 g, 0.0212 mol) was added dropwise. The mixture was allowed to slowly warm to room temperature and stirred overnight. The mixture was then cooled to 0° C. and treated with saturated aqueous ammonium chloride solution (17 mL). The mixture was extracted with dichloromethane. The extract was then washed with water and dried over magnesium sulfate. The solution was concentrated in vacuo to a dark brown oil. The oil was purified by column chromatography using 25% ethyl acetate/hexanes as eluents. Fractions containing the desired product were collected and concentrated in vacuo to yield 0.025 g (3%) of Compound 44, (Z)-1-[1-(6-chloropyridin-3-yl)cyclopropyl]-2-nitroethylenamine, as a light orange solid.

Example 45

Preparation of Compound 45

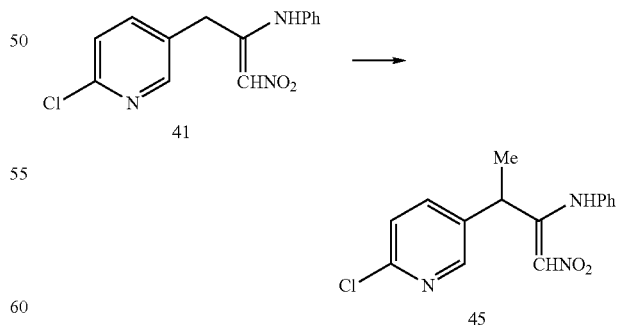

To a mixture cooled in dry ice/acetone of 234 mg (0.81 mmol) of Compound 41 in 2 mL of tetrahydrofuran was added dropwise via syringe 1.78 mL (1.78 mmol) of a 1.0M solution of lithium bis(trimethylsilyl)amide in tetrahydrofuran. After stirring for one hour, 0.275 mL (4.4 mmol) of methyl iodide was added and the contents were allowed to warm to room temperature (about 22° C.) overnight. The solution was then chilled in ice and was treated with 5 mL of saturated ammonium chloride and the mixture was then extracted with ethyl ether/ethyl acetate. The layers were separated, the organic phase was washed with brine and was dried (magnesium sulfate). Concentration gave 360 mg of a residue which was chromatographed on silica gel using gradient elution from dichloromethane to 10% ethyl acetate to give 65 mg (26%) of Compound 45, N-{(Z)-1-[1-(6-chloro-3-pyridinyl) ethyl]-2-nitroethenyl}aniline, as a solid, mp 93-95° C.; $^1$H NMR δ 1.46 (d, 3H, J=7.4 Hz), 4.04 (q, 1H, J=7.3 Hz), 6.74 (s, 1H), 7.02 (m, 2H), 7.25 (d, 1H, J=7.6 Hz), 7.36-7.40 (m, 4H), 7.83 (d, 1H, J=2.3 Hz), 11.5 (br s, 1H); MS (ESI−) m/z 304 ([M+2-H]$^+$, 29), 302 ([M−H]$^+$, 83), 255 (100). Anal. Calcd. for $C_{15}H_{14}ClN_3O_2$: C, 59.31; H, 4.64; N, 13.83. Found: C, 59.23; H, 4.57; N, 13.62.

Example 46

Preparation of Compound 46

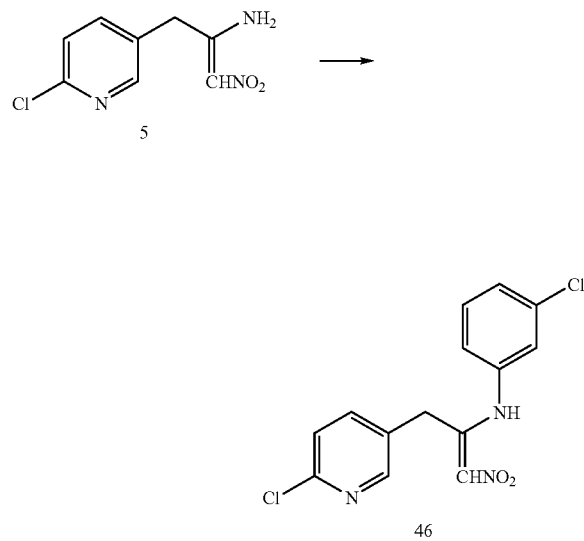

A mixture of 600 mg (2.81 mmol) of Compound 5, 358 mg (2.81 mmol) of 3-chloroaniline, and 653 mg (2.81 mmol) of camphor sulfonic acid in 8 mL of 1,2-dichloroethane was stirred for 4 days at room temperature (about 22° C.), was diluted with dichloromethane, and was washed twice with saturated sodium bicarbonate and was dried (magnesium sulfate). Concentration gave 750 mg of a solid which was recrystallized from ethyl acetate to afford 225 mg (25%) of Compound 46, 3-chloro-N-{(Z)-1-[(6-chloro-3-pyridinyl) methyl]-2-nitroethenyl}aniline, as a yellow solid, mp 133-134° C.; $^1$H NMR δ 3.58 (s, 2H), 6.59 (s, 1H), 6.94 (m, 1H), 7.10 (m, 1H), 7.26 (d, 1H, J=8.0 Hz), 7.29-7.37 (m, 3H), 7.90 (d, 1H, J=1.8 Hz), 11.2 (br s, 1H); MS (ESI+) m/z 328 ([M+4+H]$^+$, 10), 326 ([M+2+H]$^+$, 73), 324 ([M+H]$^+$, 100). Anal. Calcd. for $C_{14}H_{11}Cl_2N_3O_2$: C, 51.87; H, 3.42; N, 12.96. Found: C, 51.74; H, 3.51; N, 12.86. The mother liquor was concentrated to an oil which was chromatographed on silica gel using 7/3 hexanes/ethyl acetate as eluent to give an additional 150 mg (16%) of Compound 46.

Example 47

Preparation of Compound 47

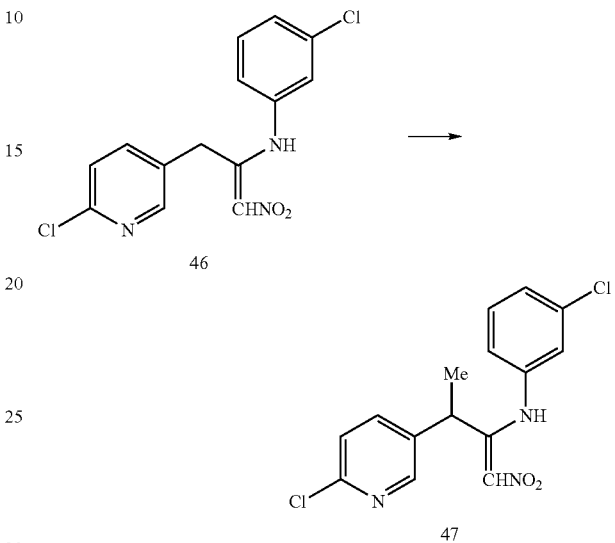

To a mixture cooled in dry ice/acetone of 320 mg (0.987 mmol) of Compound 46 in 2.5 mL of tetrahydrofuran was added dropwise via syringe 2.0 mL (2.0 mmol) of a 1.0M solution of lithium hexamethyldisilazide in tetrahydrofuran. The contents were stirred for 1.5 hours and were then treated with 0.3 mL (4.8 mmol) of methyl iodide and were allowed to gradually warm to room temperature (about 22° C.) and stir overnight. The mixture was added to 40 mL of ice water, the pH was adjusted to 6-7 with 2.0N hydrochloric acid, and was then extracted twice with ethyl acetate. The combined extracts were dried (magnesium sulfate) and concentrated to give 400 mg of a residue which was chromatographed on silica gel using gradient elution from dichloromethane to 5% ethyl acetate to afford 115 mg (34%) of Compound 47, 3-chloro-N-{(Z)-1-[1-(6-chloro-3-pyridinyl)ethyl]-2-nitroethenyl}aniline, as a pale yellow solid, mp 132.5-133.5° C.; $^1$H NMR δ 1.47 (d, 3H, J=7.0 Hz), 4.00 (q, 1H, J=7.3 Hz), 6.75 (s, 1H), 6.88 (m, 1H), 7.04 (m, 1H), 7.28-7.39 (m, 4H), 7.88 (d, 1H, J=2.6 Hz), 11.3 (br s, 1H); MS (ESI+) m/z 342 ([M+4+H]$^+$, 6), 340 ([M+2+H]$^+$, 59), 338 ([M+H]$^+$, 100). Anal. Calcd. for $C_{15}H_{13}Cl_2N_3O_2$: C, 53.27; H, 3.87; N, 12.42. Found: C, 53.24; H, 4.00; N, 12.32

Example 48

Preparation of Compound 48

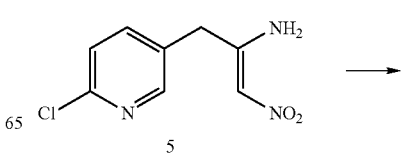

-continued

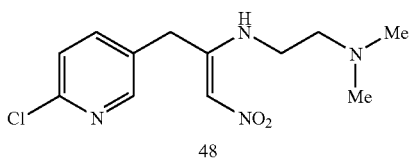
48

A round-bottomed flask charged with Compound 5 (0.498 g, 0.00235 mol) in tetrahydrofuran (10 mL) was treated with N,N-dimethylethylenediamine (0.229 g, 0.00260 mol). The flask was put under nitrogen, and the mixture was stirred at room temperature (about 22° C.) overnight. Two additional equivalents (0.414 g, 0.00470 mol) of N,N-dimethylethylenediamine was added, and the mixture was stirred for an additional 60 hours. The mixture was concentrated in vacuo to yield 0.674 g (97%) of Compound 48, N'-{(Z)-1-[(6-chloropyridin-3-yl)methyl]-2-nitrovinyl}-N,N-dimethylethane-1,2-diamine, as a yellow solid.

Example 49

Preparation of Compound 49

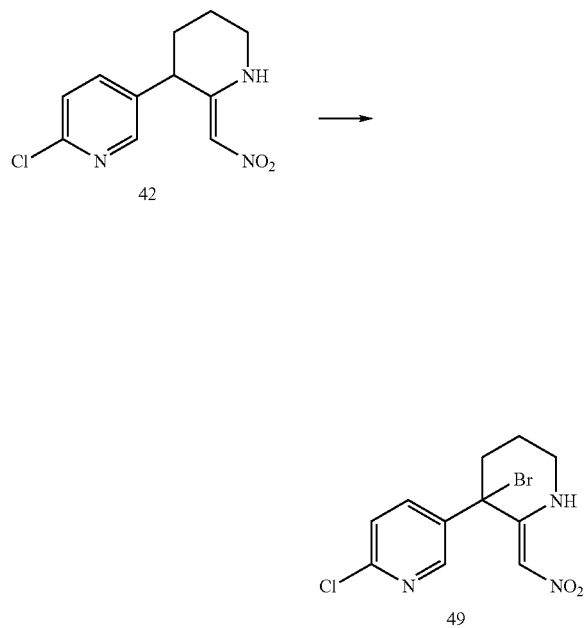

A round-bottomed flask charged with Compound 42 (0.322 g, 0.00127 mol) in chloroform (20 mL) was treated with N-bromosucciniamide (0.265 g, 0.00149 mol) and stirred at room temperature (about 22° C.) for 4.5 hours. The mixture was concentrated in vacuo to afford a dark amber oil. The oil was purified by column chromatography using 20% ethyl acetate/dichloromethane as eluents. Fractions containing the desired product were collected and concentrated in vacuo to yield 0.140 g (33%) of Compound 49, 5-[(2Z)-3-bromo-2-(nitromethylene)piperidin-3-yl]-2-chloropyridine, as a yellow oil.

Example 50

Preparation of Compound 50

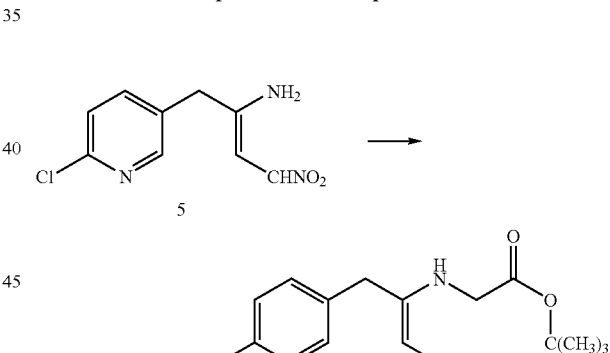

A solution of 1.07 g (5.01 mmol) of Compound 5 and 890 mg (5.00 mmol) of N-bromosuccinimide in 25 mL of chloroform was stirred at room temperature (about 22° C.) for 3 hours and was filtered to afford 1.4 g (96%) of Compound 50, (1E)-1-bromo-3-(6-chloro-3-pyridinyl)-1-nitro-1-propen-2-amine, as a yellow solid, mp 112° C. (dec).

Example 51

Preparation of Compound 51

A round-bottomed flask charged with Compound 5 (0.500 g, 0.00236 mol) in tetrahydrofuran (10 mL) was treated with glycine tert-butyl ester (0.310 g, 0.00236 mol). The mixture was stirred at room temperature (about 22° C.) overnight. An additional equivalent (0.310 g, 0.00236 mol) of glycine tert-butyl ester was added, and the mixture was stirred at 40° C. overnight, then heated at 50° C. for an additional 24 hours. The mixture was concentrated in vacuo to afford an orange solid, which was purified by column chromatography using first 5% methanol/dichloromethane, followed by 20% ethyl acetate/dichloromethane as eluents. Fractions containing the desired product were combined and concentrated in vacuo. The residue was dissolved in dichloromethane and washed with 1.5 equivalents of 1.0 N HCl and dried over magnesium sulfate. The solution was concentrated in vacuo and recrystallized from hot ethyl acetate/hexanes to yield 0.040 g (5%)

of Compound 51, tert-butyl ({(Z)-1-[(6-chloropyridin-3-yl)methyl]-2-nitrovinyl}amino)acetate, as a yellow solid. m.p. 146-147° C.

Example 52

Preparation of Compound 52

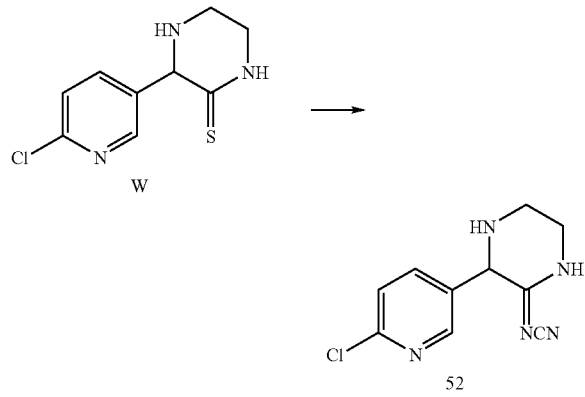

To a mixture cooled in an ice-salt bath of 146 mg (0.641 mmol) of Preparatory Compound W in 1 mL of tetrahydrofuran was added dropwise via syringe 0.63 mL (0.63 mmol) of a 1.0M solution of potassium t-butoxide in t-butanol. After 0.5 h approximately 40 µL (0.64 mmol) of methyl iodide was added and the mixture was allowed to warm to room temperature and stir for 18 h. The mixture was filtered and the filtrate was concentrated to an oil which was identified as the S-methylthioimidate of Preparatory Compound W ($^1$HNMR: 2.44 ppm 3H-singlet, MS: 242, M+H ion, electrospray positive mode). This oil was then treated with a solution of 100 mg (2.38 mmol) of cyanamide in absolute ethanol and the mixture was stirred for 18 h at room temperature. The mixture was concentrated and the residue was partitioned between dichloromethane and 10% aqueous potassium carbonate. The layers were separated, the aqueous phase was extracted once with dichloromethane and the combined organics were dried over potassium carbonate. Concentration gave 100 mg of an oil which was chromatographed on silica gel (230-400 mesh) using 9/1 dichloromethane/methanol containing 5% ammonium hydroxide to afford 9 mg (6%) of Compound 523-(6-chloro-3-pyridinyl)-2-piperazinylidenecyanamide; $^1$HNMR (CDCl$_3$) δ 8.43 (d, 1H, J=2.6 Hz), 7.93 (br s, 1H), 7.70 (dd, 1H, J=8.2 Hz, and J=2.3 Hz), 7.34 (d, 1H, J=7.9 Hz), 4.71 (br s, 1H), 3.55-3.69 (m, 1H), 3.47-3.54 (m, 1H), 3.10-3.30 (m, 2H), 2.02 (br s, 1H); MS (ES+) m/z 236 ([M+H]$^+$); IR (neat) ν cm$^{-1}$ 2193 (CN).

Biological Testing of Compounds 1-51

Compounds 1-51 were tested in the following tests.

Control of Cotton Aphid (*Aphis gossypii*)

Plant Preparation and Infestation

Hybrid squash plants (*Cucurbita pepo* cv. Pic-N-Pic) are grown under greenhouse conditions to seedling stage in 3-inch pots containing Metro Mix™. When plants have reached the expanded cotyledons stage, they are pruned to a single cotyledon. All stages of cotton aphids are transferred to the seedlings by placing infested leaf sections on top of each seedling cotyledon 16-24 hours prior to the application of the test material. As the infested sections dry out, the aphids move to the succulent plant material. The dried leaf sections are removed and plants are examined to verify adequate infestation prior to application of experimental compounds.

Spray Solution Preparation and Application

A single stock solution of technical material for each experimental compound is prepared by dissolving each material in 1 milliliter of 90:10 acetone:ethanol. One milliliter of this stock solution is then diluted in 19 milliliters water containing 0.05% of the surfactant Tween 20 to form a 50-ppm spray solution. A ten-fold dilution spray solution is then prepared by transferring 2 milliliters of the 50 ppm solution into 18 milliliters of water containing 0.05% of the surfactant Tween 20, to form a 5 ppm spray solution.

Application is made with a hand-held DeVilbiss™, airbrush sprayer. The squash cotyledons are sprayed on both the upper and lower surfaces of the cotyledon until runoff and then all the plants within the treatment are sprayed evenly until the remaining spray solution is completely used. Each rate has 4 reps (plants). Controls consist of 8 plants treated with diluent prepared with a blank stock solution only.

Holding and Grading

Test plants are held for 72 hours at approximately 74° F. and 40% relative humidity with a 24-hour photoperiod, prior to grading. The effectiveness of the applications is assessed 3 days after application by counting the live aphids (all non-winged stages) on the underside of each cotyledon using a dissecting binocular microscope. Live count results are used to calculate a percent control based on comparison of the aphid population results from the experimental treatments compared to the aphid population on the controls.

Control of Green Peach Aphid (*Myzus persicae*)

Plant Preparation and Infestation

Head cabbage (*Brassica oleracea* cv. Early Jersey Wakefield) is grown under greenhouse conditions to seedling stage in 3-inch pots containing Metro Mix™. When plants reach the 2-4 true leaf stage (approximately 12 days old), they are infested with all stages of Green peach aphid *Myzus persicae*. Infestation occurs 4 days prior to the application of the test materials. During the infestation interval, aphids move to the succulent plant material and settle to feed, predominantly on the underside of the leaves. The plants are examined to verify adequate infestation prior to application of experimental compounds.

Spray Solution Preparation and Application

A single stock solution of technical material for each experimental compound prepared, as above, by dissolving each material in 1 milliliter of 90:10 acetone:ethanol is used to prepare spray solutions for this bioassay. One milliliter of the prepared stock solution is diluted in 19 milliliters of tap water containing 0.05% of the surfactant Tween 20 to form a 50-ppm spray solution.

Application to the infested plants is made with a hand-held DeVilbiss™, airbrush sprayer. The infested cabbage seedlings are sprayed on both the upper and lower surfaces of the leaves until runoff and then all plants within the treatment are sprayed evenly until the remaining spray solution is completely used. Each treatment consists of 4 replicates (plants). The control treatments consist of 8 replicates treated with diluent prepared with a blank stock solution only.

Holding and Grading

Test plants are held 72 hours at approximately 23° C., 40% relative humidity and 24 hour photo period prior to grading. The effectiveness of the applications is assessed 3 days after application by counting the live aphids (all non-winged stages) on the underside of each leaf using a dissecting binocular microscope. Live count results are used to calculate a percent control based on comparison of the aphid population results from the experimental treatments compared to the aphid population on the controls.

Control of Sweet Potato Whitefly (*Bemisia tabaci*)

Four mg of each test compound are dissolved by adding 4 mL of a 90:10 acetone:ethanol solvent mixture to the vial containing the sample compound. This solution is added to 16 mL of water containing 0.05% Tween 20 surfactant to produce 20 mL of a 200 ppm spray solution.

Five-week-old cotton plants reared in a greenhouse are stripped of all foliage except for the two uppermost true leaves that were greater than 5 cm in diameter. These plants are then placed into a laboratory colony of whiteflies for two days, exposing the leaves to oviposition by colony females. Adult whiteflies are then removed from the test plants with pressurized air. The spray solution is then applied to the test plants with a hand-held syringe fitted with a hollow cone nozzle. One mL of spray solution is applied to each leaf surface (upper and lower) for a total of 4 mL per plant. Plants are air dried and then placed in a holding chamber (30° C. and 60% relative humidity).

At 12-13 days after application, compound efficacy is evaluated by counting the number of large nymphs ($3^{rd}$-$4^{th}$ instars) on each leaf using an illuminated magnifying lens. Percent control is based on reduction of mean number of large nymphs per leaf of treated plants relative to that observed in the solvent check (no test compound).

Control of *Nilaparvata lugens* (Brown Planthopper) and *Nephotettix cincticeps* (Green Leafhopper) by Foliar Spray Assay Experimental Procedure A stock solution of 10,000 ppm is prepared by dissolving 10 mg of technical material in 1 mL. Within a 10-mL volumetric flask, a 200 ppm solution is made by adding 1.05 mL of acetone to 0.2 mL of 10,000 ppm stock; water (8.93 mL) is then added to the level. Within a 5-mL volumetric flask, a 50 ppm solution is made by adding 0.47 mL of acetone to 1.25 mL of the previously-made 200 ppm solution; water (4.39 mL) is then added to the level.

Each replicate of the test area is prepared as follows. Three to five four-week old rice seedlings, placed in water in glass cylinders (lower end closed, upper end open) of 3 cm diameter and height of 5 cm. Within each cylinder, roots of seedlings are submerged in the water, with the plants being suspended and held by a circular piece of metal screen wrapped around the stems of the seedlings. Another glass cylinder (both ends open) of 3 cm diameter and height of 18 cm is placed on top of the first cylinder, and affixed to it with cellophane tape.

After preparation of the test area, application of the compounds is made. A finely-atomized volume of 0.5 mL of test solution is applied to the seedlings and the interior of the upper glass cylinder using a venturi-type sprayer driven by compressed air. Plants are then allowed to air dry for a minimum of 3 hr.

After spray residue has dried, test arenas are infested. Five laboratory-reared $3^{rd}$ instar nymphs of either brown planthopper or green leafhopper are introduced into the upper cylinder. A cap containing a screen is then placed over the top of the upper cylinder.

The cylinders (four replicates per treatment) are held in a growth chamber at 28° C. and 75% relative humidity, with a photoperiod of 14 hours. Mortality is observed 6 days after infestation of insects into the test arena.

Control of *Nilaparvata lugens* (Brown Planthopper) and *Nephotettix cincticeps* (Green Leafhopper) by Root Systemic Assay Experimental Procedure A stock solution of 10,000 ppm is prepared by dissolving 10 mg of technical material in 1 mL. Within a 100-mL volumetric flask, a 10 ppm solution is made by adding 3.9 mL of acetone to 0.1 mL of 10,000 ppm stock; water (96 mL) is then added to the level. Within a separate 100-mL volumetric flask, a 1 ppm solution is made by adding 3.94 mL of acetone to 0.5 mL of the previously-made 10 ppm solution; water (96.04 mL) is then added to the level.

Twenty-five mL of either 10 or 1 ppm test solution are then added to each of four glass cylinders (lower end closed, upper end open) of 3 cm diameter and height of 5 cm. Within each cylinder, roots of three to five four-week old rice seedlings are submerged in the test solution, the plants being suspended and held by a circular piece of metal screen wrapped around the stems of the seedlings.

Another glass cylinder (both ends open) of 3 cm diameter and height of 18 cm is placed on top of the first cylinder, and affixed to it with cellophane tape. Five laboratory-reared $3^{rd}$ instar nymphs of either brown planthopper or green leafhopper are introduced into the upper cylinder. A cap containing a screen is then placed over the top of the upper cylinder.

The cylinders (four replicates per treatment) are held in a growth chamber at 28° C. and 75% relative humidity, with a photoperiod of 14 hours. Mortality is observed 6 days after infestation of insects into the test arena.

Control of Beet Armyworm (*Spodoptera exigua*), Tobacco Budworm (TBW, *Heliothis virescens*), and Cabbage Looper (CL, *Trichoplusia ni*)

Technical synthetic organic entities were formulated at 400 ppm in 2 acetone:1 tap water. A 25 ppm solution was then prepared from the 400 ppm stock. Cypermethrin was used as a standard for comparison and was formulated at 6.25 ppm in 2 acetone: 1 water. 250 µL of each rate of each compound was pipetted upon the surface of 8 mL of lepidopteran diet (modified Shorey) contained in each of ten one-ounce plastic cups (one cup=1 replication).

A second-instar beet armyworm was placed upon the treated diet in each cup once the solvent had air-dried. The solutions remaining after completing applications to the one-ounce cups were then used as leaf-dip solutions for 3.5 cm leaf discs cut from cabbage leaves and cotton cotyledons.

Ten discs of each type of plant were dipped until thoroughly coated into each rate of each compound (=10 replications of each treatment). After air-drying, the treated leaf discs were placed individually into one-ounce plastic cups. Each dried, treated cotton cotyledon disc was infested with a $2^{nd}$ instar tobacco budworm larva, and each cabbage leaf disc was infested with a $2^{nd}$ instar cabbage looper larva.

Cups containing the treated substrates and larvae were capped and then held in a growth chamber at 25° C., 50-55% relative humidity, and 14 hours light:10 hours dark for 5 days. The number of dead insects of 10 per species per treatment was then determined.

In the Table below, the headings have the following meanings.

\# means Compound Number.
T-1 means Cotton Aphid Testing at 50 ppm.
T-2 means Cotton Aphid Testing at 5 ppm.
T-3 means Green Peach Aphid Testing at 50 ppm.
T-4 means Sweetpotato Whitefly Testing at 200 ppm.
T-5 means Brown Planthopper Root Systemic Testing at 10 ppm.
T-6 means Brown Planthopper Root Systemic Testing at 1 ppm.
T-7 means Brown Planthopper Foliar Spray Testing at 200 ppm.
T-8 means Brown Planthopper Foliar Spray Testing at 50 ppm.
T-9 means Green Leafhopper Root Systemic Testing at 10 ppm.
T-10 means Green Leafhopper Root Systemic Testing at 1 ppm.
T-11 means Green Leafhopper Foliar Spray Testing at 200 ppm.
T-12 means Green Leafhopper Foliar Spray Testing at 50 ppm.
T-13 means Tobacco Budworm Testing at 400 ppm.
T-14 means Tobacco Budworm Testing at 25 ppm.
T-15 means Beet Armyworm Testing at 400 ppm.
T-16 means Beet Armyworm Testing at 25 ppm.
T-17 means Cabbage Looper Testing at 400 ppm.
T-18 means Cabbage Looper Testing at 25 ppm.
G means good control observed.
P means poor control observed.
N means compound was not tested.

| # | T-1 | T-2 | T-3 | T-4 | T-5 | T-6 | T-7 | T-8 | T-9 | T-10 | T-11 | T-12 | T-13 | T-14 | T-15 | T-16 | T-17 | T-18 |
|---|---|---|---|---|---|---|---|---|---|---|---|---|---|---|---|---|---|---|
| 1 | G | G | P | P | P | P | G | P | P | P | G | P | G | P | P | P | G | P |
| 2 | G | G | G | G | G | P | G | P | G | P | G | P | G | P | P | P | G | G |
| 3 | G | P | P | P | P | P | P | P | P | P | P | P | P | P | P | P | P | P |
| 4 | G | P | P | P | P | P | P | P | P | P | P | P | P | P | P | P | P | P |
| 5 | G | G | P | P | P | P | P | P | P | P | P | P | P | P | P | P | P | P |
| 6 | G | G | P | G | P | P | P | P | P | P | G | P | P | P | P | P | P | P |
| 7 | G | G | P | G | N | N | N | N | N | N | N | N | P | P | P | P | P | P |
| 8 | G | G | P | N | P | P | P | P | P | P | G | P | P | P | P | P | P | P |
| 9 | G | G | P | P | N | N | N | N | N | N | N | N | P | P | P | P | P | P |
| 10 | G | P | P | P | N | N | N | N | N | N | N | N | P | P | P | P | P | P |
| 11 | N | N | N | N | N | N | N | N | N | N | N | N | P | P | P | P | P | P |
| 12 | G | G | G | P | P | P | P | P | P | P | G | P | P | P | P | P | P | P |
| 13 | G | P | P | P | N | N | N | N | N | N | N | N | P | P | P | P | P | P |
| 14 | G | P | P | G | N | N | N | N | N | N | N | N | P | P | P | P | P | P |
| 15 | G | G | P | G | N | N | N | N | N | N | N | N | P | P | P | P | P | P |
| 16 | G | P | P | G | N | N | N | N | N | N | N | N | P | P | P | P | P | P |
| 17 | P | P | P | P | P | P | P | P | P | P | P | P | P | P | P | P | P | P |
| 18 | P | G | P | P | P | P | P | P | P | P | P | P | P | P | P | P | P | P |
| 19 | G | P | P | P | P | P | P | P | P | P | P | P | P | P | P | P | P | P |
| 20 | G | G | P | P | P | P | P | P | G | P | G | P | P | P | P | P | P | P |
| 21 | G | G | P | P | P | P | P | P | P | P | P | P | P | P | P | P | P | P |
| 22 | G | P | P | P | P | P | P | P | P | P | P | P | P | P | P | P | P | P |
| 23 | G | G | G | P | P | P | P | P | P | P | G | P | P | P | P | P | P | P |
| 24 | G | G | N | N | N | N | N | N | N | N | N | N | P | P | P | P | P | P |
| 25 | G | G | P | G | P | P | P | P | P | P | P | P | P | P | P | P | P | P |
| 26 | P | P | P | P | P | P | P | P | P | P | P | P | P | P | P | P | P | P |
| 27 | G | P | G | G | P | P | P | P | P | P | P | P | P | P | P | P | P | P |
| 28 | G | G | P | G | P | P | G | P | P | P | G | P | P | P | P | P | P | P |
| 29 | G | P | P | P | N | N | N | N | N | N | N | P | P | P | P | P | P | P |
| 30 | N | N | N | N | N | N | N | N | N | N | N | N | N | N | N | N | N | N |
| 31 | G | P | P | G | P | P | P | P | P | P | P | P | P | P | P | P | P | P |
| 32 | G | G | P | P | P | P | P | P | P | P | P | P | P | P | P | P | P | P |
| 33 | G | P | P | P | P | P | P | P | P | P | P | P | P | P | P | P | P | P |
| 34 | G | P | P | P | G | P | P | P | P | P | P | P | P | P | P | P | P | P |
| 35 | P | P | P | P | P | P | P | P | P | P | P | P | P | P | P | P | P | P |
| 36 | G | G | P | P | P | P | P | P | P | P | P | P | P | P | P | P | P | P |
| 37 | P | P | P | P | P | P | P | P | P | P | P | P | P | P | P | P | P | P |
| 38 | P | P | P | P | P | P | P | P | P | P | P | P | P | P | P | P | P | P |
| 39 | G | G | P | P | P | P | P | P | P | P | G | P | P | P | P | P | P | P |
| 40 | G | P | P | P | P | P | P | P | P | P | P | P | P | P | P | P | P | P |
| 41 | P | P | P | P | P | P | P | P | P | P | P | P | P | P | P | P | P | P |
| 42 | G | G | G | G | G | P | G | P | P | P | G | P | G | P | P | P | G | P |
| 43 | G | G | P | P | P | P | P | P | P | P | P | P | P | P | P | P | P | P |
| 44 | G | G | G | N | N | N | N | N | N | N | N | N | P | P | P | P | P | P |
| 46 | P | P | P | P | P | P | P | P | P | P | P | P | P | P | P | P | P | P |
| 47 | P | P | P | P | N | N | N | N | N | N | N | N | P | P | P | P | P | P |
| 48 | P | P | P | P | N | N | N | N | N | N | N | N | P | P | P | P | P | P |
| 49 | G | G | G | G | N | N | N | N | N | N | N | N | P | P | P | P | P | P |
| 50 | G | G | P | P | N | N | N | N | N | N | N | N | P | P | P | P | P | P |
| 51 | P | P | P | P | N | N | N | N | N | N | N | N | P | P | P | P | P | P |

We claim:
1. A process of applying a compound of the formula

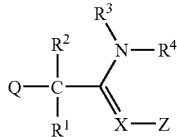

Figure One wherein

Q can be any five- or six membered heterocyclic ring,

X is N, CR, COR, CSO$_n$R (where n=0, 1, or 2), CN(R)$_2$, C(C=O)R, C(C=S)R, C(C=NR)R, CP(=O)$_m$(R)$_2$ (where m=0 or 1), or CP(=S)$_m$(R)$_2$ (where m=0 or 1), wherein each R independently can be
- (a) a $C_{1-10}$, branched or unbranched, alkyl, alkoxy, alkenyl, alkynyl, alkylthio, alkylsulfinyl, alkylsulfonyl, alkylcarbonyl, alkylcarbonothioyl, alkoxycarbonyl, alkylthiocarbonyl, alkoxycarbonothioyl, alkylthiocarbonothioyl, or HC(=NH)—,
- (b) a $C_{3-10}$, cycloalkyl, or cycloalkenyl,
- (c) an aryl, heterocyclyl, aryloxy, heterocyclyloxy, arylthio, heterocyclylthio, arylamino, or heterocyclylamino, or
- (d) a hydro, hydroxy, mercapto, amino, cyano, formyl, nitro, halo, or aminocarbonyl, Z is CN or NO$_2$, $R^1$ and $R^2$ each independently can be
- (a) a $C_{1-10}$, branched or unbranched, alkyl, alkoxy, alkenyl, alkynyl, alkylthio, alkylsulfinyl, alkylsulfonyl, alkylcarbonyl, alkylcarbonothioyl, alkoxycarbonyl, alkylthiocarbonyl, alkoxycarbonothioyl, alkylthiocarbonothioyl, or HC(=NH)—,
- (b) a $C_{3-10}$, cycloalkyl, or cycloalkenyl,
- (c) an aryl, heterocyclyl, aryloxy, heterocyclyloxy, arylthio, heterocyclylthio, arylamino, or heterocyclylamino, or
- (d) a hydro, hydroxy, mercapto, amino, cyano, formyl, nitro, halo, or aminocarbonyl, $R^1$ and $R^2$ can optionally be linked together with either a bond or a chain of 1-4 atoms, where such atoms can be carbon, nitrogen, sulfur, phosphorus and oxygen, $R^3$ and $R^4$ independently can be,
- (a) a $C_{1-10}$, branched or unbranched, alkyl, alkoxy, alkenyl, alkynyl, alkylthio, alkylsulfinyl, alkylsulfonyl, alkylcarbonyl, alkylcarbonothioyl, alkoxycarbonyl, alkylthiocarbonyl, alkoxycarbonothioyl, alkylthiocarbonothioyl, or HC(=NH)—,
- (b) a $C_{3-10}$, cycloalkyl, or cycloalkenyl,
- (c) an aryl, heterocyclyl, aryloxy, heterocyclyloxy, arylthio, heterocyclylthio, arylamino, or heterocyclylamino, or
- (d) a hydro, hydroxy, mercapto, amino, cyano, formyl, nitro, halo, or aminocarbonyl, $R^2$ and $R^3$ can optionally be linked together with a chain of 1-4 atoms, where such atoms can be carbon, nitrogen, sulfur, phosphorus and oxygen, $R^3$ and $R^4$ can optionally be linked together with a chain of 1-4 atoms, where such atoms can be carbon, nitrogen, sulfur, phosphorus and oxygen, Each member of Q, X, R, $R^1$, $R^2$, $R^3$, and $R^4$, which may have a hydrogen atom in a certain position, may instead of having such hydrogen atom, have a,
- (a) a $C_{1-10}$, branched or unbranched, alkyl, alkoxy, alkenyl, alkynyl, alkylthio, alkylsulfinyl, alkylsulfonyl, alkylcarbonyl, alkylcarbonothioyl, alkoxycarbonyl, alkylthiocarbonyl, alkoxycarbonothioyl, alkylthiocarbonothioyl, HC(=NH)—, dialkylphosphonyl, or dialkylphosphatyl,
- (b) a $C_{3-10}$, cycloalkyl, or cycloalkenyl,
- (c) an aryl, heterocyclyl, aryloxy, heterocyclyloxy, arylthio, heterocyclylthio, arylamino, or heterocyclylamino, or
- (d) a hydro, hydroxy, mercapto, amino, cyano, formyl, nitro, halo, or aminocarbonyl, in such position, to a locus in an amount effective to control pests.

2. A process of applying a compound according to claim 1, to a locus in an amount effective to control insects or mites.

3. A process of topically applying a compound according to claim 1 to an animal in an amount effective to control fleas.

4. A process of orally administering a compound according to claim 1 to an animal in an amount effective to control fleas.

* * * * *